US008759067B2

(12) United States Patent
Chi et al.

(10) Patent No.: US 8,759,067 B2
(45) Date of Patent: Jun. 24, 2014

(54) POLYNUCLEOTIDES ENCODING ENGINEERED PLANT CYSTEINE PROTEASES AND THEIR USES

(71) Applicants: Ellen Chi, San Diego, CA (US); Michael Hunter, San Diego, CA (US); Ronald Swanson, San Diego, CA (US)

(72) Inventors: Ellen Chi, San Diego, CA (US); Michael Hunter, San Diego, CA (US); Ronald Swanson, San Diego, CA (US)

(73) Assignee: Centocor Ortho Biotech Inc., Horsham, PA (US)

( * ) Notice: Subject to any disclaimer, the term of this patent is extended or adjusted under 35 U.S.C. 154(b) by 0 days.

(21) Appl. No.: 13/849,051

(22) Filed: Mar. 22, 2013

(65) Prior Publication Data

US 2013/0196413 A1 Aug. 1, 2013

Related U.S. Application Data

(62) Division of application No. 13/086,627, filed on Apr. 14, 2011, now Pat. No. 8,426,186.

(60) Provisional application No. 61/324,972, filed on Apr. 16, 2010.

(51) Int. Cl.

| | |
|---|---|
| *C12N 9/50* | (2006.01) |
| *C12N 15/00* | (2006.01) |
| *C12N 5/02* | (2006.01) |
| *C12N 1/20* | (2006.01) |
| *C12N 1/00* | (2006.01) |
| *C12N 1/12* | (2006.01) |
| *C07H 21/04* | (2006.01) |

(52) U.S. Cl.
USPC ....... 435/219; 536/23.2; 435/320.1; 435/325; 435/410; 435/252.3; 435/254.11; 435/257.2

(58) Field of Classification Search
None
See application file for complete search history.

(56) References Cited

FOREIGN PATENT DOCUMENTS

WO WO 00/20619 A2 4/2000

OTHER PUBLICATIONS

Aharoni, et al., "The 'evolvability' of promiscuous protein functions," Nature Genetics, 37(1): 73-76 (2005).
Anindya, et al.Potyviral NIa Proteinase, a Proteinase with Novel Deoxyribonuclease Activity, The Journal of Biological Chemistry, 279(31): 32159-32169 (2004).
Bazan, et al., "Viral cysteine proteases are homologous to the trypsin-like family of serine proteases: Structural and functional implications," Proceedings of the National Academy of Science USA, 85: 7872-7876 (1988).
Birch, et al., "Purification of Recombinant Human Rhinovirus 14 3C Protease Expressed in *Escherichia coli*," Protein Expression and Purification, 6: 609-618 (1996).
Dougherty, et al., "Molecular Genetic Analysis of a Plant Virus Polyprotein Cleavage Site: A Model" Virology, 171: 356-364 (1989).
Dougherty, et al., "Biochemical and mutational analysis of a plant virus polyprotein cleavage site," The EMBO Journal, 7(5): 1281-1287 (1988).
Gosalia, et al., "High Throughput Substrate Specificity Profiling of Serine and Cysteine Proteases Using Solution-phase Flurorgenic Peptide Microarrays," Molecular & Cellular Proteomics, 4: 626-636 (2005).
Higaki, et al., "Evolution of Catalysis in the Serine Proteases," Cold spring harbor Symposia on Quantitative Biology, 52: 615-621 (1987).
Kekarainen, et al., "Comparison of the complete sequences of five different isolated of *Potato virus A* (PVA), genus *Potyvirus*," Archives of Virology, 144: 2355-2366 (1999).
Mastumura, et al., "In vitro Evolution of Beta-glucuronidase into a Beta-galactosidease Proceeds Through Non-Specific Intermediates," Journal of Molecular Biology, 305: 331-339 (2001).
Nunn, et al., "Crystal Structure of Tobacco Etch Virus Protease Shows the Protein C Terminus Bound within the Active Site," Journal of Molecular Biology, 350: 145-155 (2005). Parks, et al., "Expression and Purification of a Recombinant Tobacco Etch Virus Nia Proteinase: Biochemical Analyses of the Full-Length and a Naturally Occurring Truncated Proteinase Form," Virology, 210: 194-201 (1995).
Rothman, et al., "How Does an Enzyme Evolved In vitro Compare to Naturally Occurring Homologs Possessing the Targeted Function? Tyrosine Aminotransferase from Aspartate Aminotransferase," Journal of Molecular Biology, 327: 593-608 (2003).
Tözser, et al., "Comparison of the substrate specificity of two potyvirus proteases," FEBS Journal, 272: 514-523 (2005).
Verchot, et al., "Mutational Analysis of the Tobacco Etch Potyviral 35-kDa Proteinase: Identification of Essential Residues and Requirements for Autoproteolysis," Virology, 190: 298-306 (1992).
Walker, et al., "Enzyme Engineering—The Design and Construction of Novel Enzymes," Molecular Biology and Biotechnology, London, Royal Society of Chemistry, Chapter 17: 377-388 (1989).

*Primary Examiner* — David J Steadman
(74) *Attorney, Agent, or Firm* — Kirk Baumeister

(57) ABSTRACT

The present invention relates to potato virus NIa protease variants or fragments thereof, polynucleotides encoding them, and methods of making and using the foregoing.

6 Claims, No Drawings

POLYNUCLEOTIDES ENCODING ENGINEERED PLANT CYSTEINE PROTEASES AND THEIR USES

CROSS-REFERENCE TO RELATED APPLICATIONS

This application is a divisional of U.S. application Ser. No. 13/086,627, filed 14 Apr. 2011 which claims priority to U.S. Provisional Application Ser. No. 61/324,972, filed 16 Apr. 2010, the entire contents of which is incorporated herein by reference in its entirety.

FIELD OF THE INVENTION

The present invention relates to potato virus NIa protease variants or fragments thereof, polynucleotides encoding them, and methods of making and using the foregoing.

BACKGROUND OF THE INVENTION

Considerable effort has been employed to engineer enzymes and other proteins to achieve higher selectively and/or specific activity (Matsumura and Ellington, J. Mol. Biol. 305:331-339, 2001; Rothman and Kirsch, J. Mol. Biol. 327: 593-608, 2003; Aharoni et al., Nature Genetics, 37:73-76, 2005). Human trypsin-like serine proteases are an appealing target for engineering with the goal to tailor proteases to recognize a specific, predefined primary sequence within a target protein that is normally not recognized, resulting in specific spatial and temporal modulation of target activity. Trypsin-like serine proteases are also valuable research tools in molecular biology.

Manufacturing of trypsin-like serine proteases poses challenges due to their structural complexity related to the required appropriate disulfide bond formation and proper processing of the native globular polypeptide chain for activity. Furthermore, trypsin-like serine proteases often have a constricted recognition sequence limiting the absolute specificity that can be engineered into the molecules. (Gosalia et al., Mol. Cell. Proteomics, 4:626-36, 2005, US Pat. Appl. No. US20040072276A1). An alternative to human trypsin-like serine proteases, intracellular plant viral proteases that are easier to manufacture could be used as a starting point to develop therapeutics as well as new research tools.

Potyviruses are a class of plant viruses transmitted mainly by aphids, causing significant losses in pasture, agricultural, horticultural and ornamental crops annually. Typical representatives of potyviruses are Potato virus A (PVA), tobacco etch virus (TEV) and tobacco vein mottling virus (TVMV). Potyvirus monopartite genome contains (+) stranded RNA, covalently linked to a viral encoded protein (VPg) at the 5'-end and polyadenylated at the 3'-end (Dougherty et al., The EMBO J. 7:1281-1287, 1988). The genome serves as an mRNA and a template for the synthesis of a complementary (−) stranded RNA by a polymerase translated from the viral genome. Upon entry into the cell, the virus RNA binds to endogenous ribosomes and the genome is translated as a single polypeptide chain. The large single polyprotein is subsequently processed into mature proteins by three virus-encoded proteases (Verchot et al., Virology, 190:298-306, 1992), the first protein (P1), the helper component (HC), and the nuclear inclusion protein (NIa) proteases. The NIa protease is responsible for the majority of the polyprotein processing, including the generation of mature RNA replication-associated proteins and capsid proteins (Verchot et al., Virology, 190:298-306, 1992).

The NIa proteases belong to the family of picornavirus 3C cysteine proteases (Parks et al., Virology, 210:194-201, 1995), that exhibit an extended P6-P1' recognition sequence EXXYXQ*(S/G) (SEQ ID NO: 69) (Dougherty et al., Virology, 171:356-364, 1989). Although there are striking similarities in the recognition sequence for NIa proteases across the potyvirus members, each protease is highly specific for its own target sequence (Tozer et al., The FEBS J. 272:514-523, 2004). Structurally, NIa proteases appear to be related to trypsin-like serine proteases through divergent evolution involving replacement of NIa catalytic cysteine by serine in the trypsin-like proteases (Bazan and Fletterick, Proc. Natl. Acad. Sci. 85:7872-7876, 1988). NIa and trypsin-like serine proteases share a similar overall 3-dimensional protein fold as well as the spatial proximity of their respective catalytic residues. The 3C-like family of cysteine proteases offers several advantages over more complex extracellular proteases. They can be easily produced in the cytosol of bacteria, have no disulfide bonds, and have an extended substrate recognition sequence. The challenge of using the 3C-like proteases is their activity loss in non-reducing conditions due to oxidation of active site and/or surface exposed cysteines, therefore limiting their use (Higaki et al., Cold Spring Harbor Symposia on Quantitative Biology, 615-621, 1987). Therefore, the proteases require reducing agent to sustain their functional activity (Nunn et al., J. Mol. Biol. 350:145-55, 2005; Birch et al., Protein Expression and Purification 6:609-18, 1995). Thus, there is a need for engineered plant viral proteases that remain active in the absence of exogenous reducing agents.

SUMMARY OF INVENTION

One aspect of the invention is an isolated polypeptide encoding a NIa protease variant, wherein the variant is resistant to oxidation and retains activity.

Another aspect of the invention is an isolated polypeptide comprising a polypeptide having the sequence shown in SEQ ID NO: 1 having amino acid substitutions selected from the group consisting of:

a. cysteine at position 19 is substituted for serine or valine;
b. cysteine at position 110 is substituted for serine;
c. cysteine at position 151 is substituted for serine or alanine.
d. cysteine at position 181 is substituted for serine; and
e. cysteine at position 211 is substituted for serine.

Another aspect of the invention is an isolated polypeptide comprising a polypeptide having the sequence shown in SEQ ID NO: 28.

Another aspect of the invention is isolated polynucleotides encoding the polypeptides of the invention.

Another aspect of the invention is a vector comprising an isolated polynucleotide encoding a polypeptide of the invention.

Another aspect of the invention is an isolated host cell comprising the vector of the invention.

Another aspect of the invention is a method for expressing the polypeptides of the invention.

DETAILED DESCRIPTION OF THE INVENTION

All publications, including but not limited to patents and patent applications, cited in this specification are herein incorporated by reference as though fully set forth.

As used herein and in the claims, the singular forms "a," "and," and "the" include plural reference unless the context clearly dictates otherwise. Thus, for example, reference to "a polypeptide" is a reference to one or more polypeptides and includes equivalents thereof known to those skilled in the art.

Unless defined otherwise, all technical and scientific terms used herein have the same meaning as commonly understood by one of ordinary skill in the art to which an invention belongs. Although any compositions and methods similar or equivalent to those described herein can be used in the practice or testing of the invention, exemplary compositions and methods are described herein.

The term "NIa protease" as used herein refers to the potato virus A (PVA) NIa protease encoded by amino acids 2032-2264 of the virus proprotein shown in GenBank Acc. No. CAB58238. The polypeptide sequence of the NIa protease is shown in SEQ ID NO: 1.

The term "polypeptide" as used herein refers to a molecule that comprises at least two amino acid residues linked by a peptide bond to form a polypeptide. Small polypeptides of less than 50 amino acids may be referred to as "peptides". Polypeptides may also be referred as "proteins."

The term "polynucleotide" as used herein refers to a molecule comprising a chain of nucleotides covalently linked by a sugar-phosphate backbone or other equivalent covalent chemistry. Double and single stranded DNAs and RNAs are typical examples of polynucleotides.

The term "complementary sequence" means a second isolated polynucleotide sequence that is antiparallel to a first isolated polynucleotide sequence and that comprises nucleotides complementary to the nucleotides in the first polynucleotide sequence. Typically, such "complementary sequences" are capable of forming a double-stranded polynucleotide molecule such as double-stranded DNA or double-stranded RNA when combined under appropriate conditions with the first isolated polynucleotide sequence.

The term "variant" as used herein refers to a polypeptide or a polynucleotide that differs from a reference "wild type" polypeptide or a polynucleotide and may or may not retain essential properties. Generally, differences in sequences of the wild type and the variant are closely similar overall and, in many regions, identical. A variant may differ from the wild type in its sequence by one or more modifications for example, substitutions, insertions or deletions of nucleotides or amino acids. Substitutions or insertions may result in conservative or non-conservative amino acid substitutions, or in the generation of a stop codon. A variant of a polynucleotide may be naturally occurring, and may have 70%, 75%, 80%, 85%, 90%, 95%, 96%, 97%, 98%, or 99% identity with the wild type polynucleotide.

It is possible to modify the structure or function of the polypeptides encoded by variant polynucleotide sequences for such purposes as enhancing activity, specificity, stability, solubility, and the like. A replacement of a codon encoding leucine with codons encoding isoleucine or valine, a codon encoding an aspartate with a codon encoding glutamate, a codon encoding threonine with a codon encoding serine, or a similar replacement of codons encoding structurally related amino acids (i.e., conservative mutations) will, in some instances but not all, not have a major effect on the biological activity of the resulting molecule. Conservative replacements are those that take place within a family of amino acids that share chemically related side chains. Naturally occurring amino acids can be divided into four families based on their side chains: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, naturally occurring amino acids can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981). Whether a change in the amino acid sequence of a polypeptide or fragment thereof encoded by a variant polynucleotide results in a functional homolog can be readily determined by assessing the ability of the modified polypeptide or fragment to produce a response in a fashion similar to the unmodified polypeptide or fragment using the assays described herein. Peptides, polypeptides or proteins in which more than one replacement has taken place can readily be tested in the same manner.

The term "wild type" or "WT" refers to a polypeptide or a polynucleotide that has the characteristics of that polypeptide or polynucleotide when isolated from a naturally occurring source. An exemplary wild type polynucleotide is a polynucleotide encoding a gene that is most frequently observed in a population and is thus arbitrarily designated the "normal" or "reference" or "wild type" form.

The term "activity" or "active" as used herein refers to an active NIa protease, e.g., a NIa protease capable of cleaving its substrate. Exemplary substrates are synthetic peptides corresponding to identified recognition sequences, for example SEVVLFQASS (SEQ ID NO: 70), SEAVYTQGSS (SEQ ID NO: 71), or SENVTFQGSS (SEQ ID NO: 72), as described in Table 5. and in Mertis et al., (Mertis et al., J. Gen. Virol. 83:1211-1221, 2002). Partial cleavage of the substrate is sufficient for effective biological activity of the protease, for example cleavage of 50%, 60%, 70%, 80%, 90%, 95%, or 99% of a substrate. Thus, biological activity does not require complete cleavage of the substrate. "Partially active" refers to a NIa protease that partially cleaves its substrate.

The term "resistant to oxidation" or "oxidation resistant" as used herein means that the NIa protease variant is active and functionally stable in the absence of a reducing agent that is required for functional stability of the wild type NIa protease. The reducing agent required for the activity of the wild type NIa protease can be dithiotreitol (DTT), 2-mercaptoethanol or tris carboxyethylphosphate (TCEP), typically in the range of 0.1-10 mM.

"Heterologous amino acid sequence" as used herein refers to an amino acid sequence not naturally fused to the NIa protease polypeptide. Heterologous amino acid sequences can be attached to either the N- or C-terminus of the NIa protease polypeptide using standard methods. The heterologous sequences can be used to provide a tag for fusion protein purification, such as attachment of polyhistidine or glutamine S-transferase tags, or to increase half life of the NIa protease, such as attachment of a constant domain of an immunoglobulin or albumin, or fragments thereof. Heterologous amino acid sequences can be fused to the polypeptide using well known methods, for example chemical coupling, or via an amide bond. An immunoblogulin hinge or a fragment thereof, a fragment of a variable region of an immunoglobulin, or a linker can also be fused to the NIa protease polypeptide.

The term "vector" means a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, bacteria, animal, plant, and reconstituted biological systems utilizing biological components capable of duplicating a vector. The polynucleotides comprising a vector may be DNA or RNA molecules or hybrids of these.

The term "expression vector" means a vector that can be utilized in a biological system or a reconstituted biological system to direct the translation of a polypeptide encoded by a polynucleotide sequence present in the expression vector.

The present invention provides NIa protease variants that are resistant to oxidation, polynucleotides encoding the variants, vectors comprising these polynucleotides, isolated host cells, methods for expressing the polypeptides of the invention, and methods of using the polynucleotides and polypeptides of the invention. The variants of the invention are useful as research tools, and can be used, e.g., to cleave fusion proteins to remove tags.

One embodiment of the invention is an isolated polypeptide encoding a NIa protease variant, wherein the variant is resistant to oxidation and retains its activity. In oxidizing conditions, i.e., in the absence of a reductant, the wild type NIa aggregates and becomes inactive (Example 1).

In another embodiment, the NIa protease variant resistant to oxidation and retaining its activity has at least one cysteine residue substituted. Other variants may have 2, 3, 4 or 5 cysteine residues substituted. The wild type NIa protease shown in SEQ ID NO: 1 has a total of five cysteines: one active site cysteine at position 151, and four cysteines at positions 19, 110, 181 and 211 which, based on crystal structure predictions are on the surface of the protease and thus susceptible to oxidation. Exemplary substitutions are substitutions for serine, valine or alanine. Sequences of exemplary NIa protease variants are shown in Table 2.

Variants of the invention can be made by well known methods, for example site-directed or random mutagenesis (Kunkel, Proc. Natl. Acad. Sci. USA, 82:488-492, 1985; Weiner et al., Gene, 151:119-123, 1994; Ishii et al., Methods Enzymol., 293:53-71, 1988), or by chemical synthesis (U.S. Pat. No. 6,670,127, U.S. Pat. No. 6,521,427). Rational design can be employed to design variants anticipated to have specific effect on structure or activity of the wild type protease. Whether a change in the amino acid sequence of a polypeptide or fragment thereof results in a functional homolog can be readily determined by assessing the ability of the variant polypeptide or fragment to produce a response in a fashion similar to the wild type polypeptide or fragment using the assays described herein. Peptides, polypeptides or proteins in which more than one replacement has taken place can readily be tested in the same manner. Exemplary assays assessing protease activity measure fluorescence released by a fluorophore/quencher substrate peptide such as 4-(4-dimethylaminophenylazo)benzoyl (DABCYL)-YGENVTFQGSK-5-[(2-aminoethyl)amino]naphthalene-1-sulfonic acid (EDANS) (SEQ ID NO: 73) upon proteolysis, or evaluate cleavage of a peptide substrate on SDS-PAGE after protease cleavage.

The polypeptides of the invention may be produced by chemical synthesis, such as solid phase peptide synthesis on an automated peptide synthesizer. Alternatively, the polypeptides of the invention can be obtained from polynucleotides encoding these polypeptides by the use of cell-free expression systems such as reticulocyte lysate based expression systems or by expression and isolation from cells harboring a nucleic acid sequence of the invention by well known techniques, such as recombinant expression of easily isolated affinity labeled polypeptides.

Another embodiment of the invention is an isolated polypeptide comprising a polypeptide having the sequence shown in SEQ ID NO: 1 having substitutions selected from the group consisting of:
  a. cysteine at position 19 is substituted for serine or valine;
  b. cysteine at position 110 is substituted for serine;
  c. cysteine at position 151 is substituted for serine or alanine.
  d. cysteine at position 181 is substituted for serine; and
  e. cysteine at position 211 is substituted for serine.

The polypeptides of the invention may comprise fusion polypeptides comprising a polypeptide of the invention fused with a heterologous polypeptide. Such heterologous polypeptides may be leader or secretory signal sequences, a pre- or pro- or prepro-protein sequence, a Histidine tag (His-tag) (Gentz et al., Proc. Natl. Acad. Sci. (USA) 86:821-284, 1989), the HA peptide tag (Wilson et al., Cell 37:767-778, 1984), glutathione-S-transferase, fluorescent tags such as green fluorescent protein (GFP), and the like. Exemplary NIa protease variant-His-tag fusion proteins have amino acid sequences shown in SEQ ID NOs: 37, 38 or 39. In one aspect, the NIa protease variant polypeptide is fused to an immunoglobulin constant domain or a fragment thereof. Such constructs are well known and are described in e.g. U.S. Pat. No. 5,116,964, U.S. Pat. No. 5,709,859, U.S. Pat. No. 6,018,026; WO 04/002417; WO 04/002424; WO 05/081687; and WO 05/032460. Immunoglobulin constant domain may be a CH1, CH2, or a CH3 domain, or a hinge region, and can be derived from IgG1, IgG2, IgG3, IgG4, IgA, IgM, or IgA. The NIa protease variant polypeptide can be fused to an immunoglobulin constant domain or a fragment thereof via a linker, for example a glycine-rich linker, or via a fragment of an immunoglobulin variable region. Such linkers and variable region fragments are described in e.g. WO08/011,446 and U.S. Pat. No. 5,908,626. Exemplary fusion proteins can be formed by conjugating together a NIa protease variant having an amino acid sequence shown in SEQ ID NO: 28 and one or more domains derived from or similar to an immunoglobulin domain, such as CH1, CH2, and CH3 domain.

Another embodiment of an invention is an isolated polypeptide comprising a polypeptide having the sequence shown in SEQ ID NO: 28.

In another embodiment, the invention provides for an isolated polypeptide comprising a polypeptide having the sequence shown in SEQ ID NO: 28.

The polypeptides of the invention can be lyophilized for storage and reconstituted in a suitable carrier prior to use. An exemplary carrier is phosphate buffered saline. This technique has been shown to be effective with conventional protein preparations. Lyophilization and reconstitution techniques are well known in the art, see e.g., Rey and May, Drugs and the Pharmaceutical Sciences Vol. 137, 1999; Wang, Int. J. Pharm. 203:1-60, 2000. These techniques allow for the development of protein formulations with increased long term stability, including storage at room temperature, as well as easier geographical distribution. This process also affords the protein to be used at higher concentrations by adjusting the reconstitution procedure.

Another aspect of the invention is isolated polynucleotides encoding any of the polypeptides of the invention or their complement. Certain exemplary polynucleotides are disclosed herein, however, other polynucleotides which, given the degeneracy of the genetic code or codon preferences in a given expression system, encode the NIa protease variants of the invention are also within the scope of the invention.

Exemplary polynucleotides are polynucleotides comprising the nucleic acid sequence shown in SEQ ID NOs: 41-43 and 46-48.

The polynucleotides of the invention may be produced by chemical synthesis such as solid phase polynucleotide synthesis on an automated polynucleotide synthesizer. Alternatively, the polynucleotides of the invention may be produced by other techniques such a PCR based duplication, vector based duplication, or restriction enzyme based DNA manipulation techniques. Techniques for producing or obtaining polynucleotides of a given known sequence are well known in the art.

The polynucleotides of the invention may also comprise at least one non-coding sequence, such as transcribed but not translated sequences, termination signals, ribosome binding sites, mRNA stabilizing sequences, introns and polyadenylation signals.

Another embodiment of the invention is a vector comprising an isolated polynucleotide encoding polypeptides of the invention.

Another embodiment of the invention is a vector comprising an isolated polynucleotide having a sequence shown in SEQ ID NO: 42 or 47. The vectors of the invention are useful for maintaining polynucleotides, duplicating polynucleotides, or driving expression of a polypeptide encoded by a vector of the invention in a biological system, including reconstituted biological systems. Vectors may be chromosomal-, episomal- and virus-derived such as vectors derived from bacterial plasmids, bacteriophages, transposons, yeast episomes, insertion elements, yeast chromosomal elements, baculoviruses, papova viruses such as SV40, vaccinia viruses, adenoviruses, fowl pox viruses, pseudorabies viruses, picornaviruses and retroviruses and vectors derived from combinations thereof, such as cosmids and phagemids.

The vectors of the invention can be formulated in microparticles, with adjuvants, lipid, buffer or other excipients as appropriate for a particular application.

In one embodiment of the invention the vector is an expression vector. Expression vectors typically comprise nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art. Nucleic acid sequence elements and parent vector sequences suitable for use in the expression of encoded polypeptides are also well known in the art.

Another embodiment of the invention is an isolated host cell comprising a vector of the invention. Representative host cell examples include Archaea cells; bacterial cells such as Streptococci, Staphylococci, Enterococci, *E. coli*, *Streptomyces*, cyanobacteria, *B. subtilis* and *S. aureus*; fungal cells such as *Kluveromyces*, *Saccharomyces*, *Basidomycete*, *Candida albicans* or *Aspergillus*; insect cells such as *Drosophila* S2 and *Spodoptera* Sf9; animal cells such as CHO, COS, HeLa, C127, 3T3, BHK, 293, CV-1, Bowes melanoma and myeloma; and plant cells, such as gymnosperm or angiosperm cells. The host cells in the methods of the invention may be provided as individual cells, or populations of cells.

Introduction of a polynucleotide, such as a vector, into a host cell can be effected by methods well known to those skilled in the art (Davis et al., Basic Methods in Molecular Biology, 2$^{nd}$ ed., Appleton & Lange, Norwalk, Conn., 1994; Sambrook et al., Molecular Cloning: A Laboratory Manual, 3$^{rd}$ ed., Cold Spring Harbor Laboratory Press, Cold Spring Harbor, N.Y., 2001). These methods include calcium phosphate transfection, DEAE-Dextran mediated transfection, microinjection, cationic lipid-mediated transfection, electroporation, transduction, scrape loading, ballistic introduction and infection.

Another embodiment of the invention is a method for expressing a polypeptide comprising the steps of providing a host cell of the invention and culturing the host cell under conditions sufficient for the expression of at least one polypeptide of the invention. The polypeptides of the invention comprise polypeptides having an amino acid sequence shown in SEQ ID NOs: 2-34 and 37-39.

Host cells can be cultured under any conditions suitable for maintaining or propagating a given type of host cell and sufficient for expressing a polypeptide. Culture conditions, media, and related methods sufficient for the expression of polypeptides are well known in the art. For example, many mammalian cell types can be aerobically cultured at 37° C. using appropriately buffered DMEM media while bacterial, yeast and other cell types may be cultured at 37° C. under appropriate atmospheric conditions in LB media.

In the methods of the invention the expression of a polypeptide can be confirmed using a variety of different techniques well known in the art. For example, expression of a polypeptide can be confirmed using SDS page, detection reagents, such as antibodies or receptor ligands specific for an expressed polypeptide, or using for example FACS or immunofluorescent techniques.

Other features of the invention will become apparent in the course of the following descriptions of exemplary embodiments which are given for illustration of the invention and are not intended to be limiting thereof.

Example 1

Generation and Characterization of NIa Variants

Cloning and Mutagenesis

The amino acid sequence of potato virus A NIa protease (Genbank Acc. No. CAB58238, amino acids residues 2032-2263), shown in SEQ ID NO: 1, including an N-terminal poly-histidine tag for affinity purification was back translated into a cDNA sequence optimizing codon usage. The full-length cDNA was generated by parsing the sequence into smaller fragments and synthesizing these as oligonucleotides using GENEWRITER™ technology and purified by RP HPLC (Dionex, Germany). The purified oligonucleotides were then assembled into a full-length, double stranded cDNA fragment as described in U.S. Pat. No. 6,670,127 and U.S. Pat. No. 6,521,427.

The cDNA from the gene assembly process was cloned into the pET9d vector (Novagen, Madison, Wis.) into NcoI/XhoI sites using standard protocols. Mutagenesis targeting active site cysteine and surface sulfydryl changes was done using the QuikChange site-directed mutatgenesis kit (Stratagene, La Jolla, Calif.) using oligonucleotides shown in Table 1. Protein sequence alignments and the solved crystal structures of TEV NIa protease ((Allison et al., Virology 154:9-20, 1986; Phan et al., J. Biol. Chem. 277:50564-72, 2002) were used to estimate whether the unpaired cysteine residues in NIa protease were surface exposed. As they all appeared to be surface exposed, all were targeted for point mutations. As a first pass, all except the active site cysteine were changed to serine residues.

The cysteine residue at position 19 did not tolerate the serine substitution, as indicated by a lack of protein expression (see below). Consequently, position 19 was randomized using an NNK oligo in a QuikChange site-directed mutagenesis reaction using standard protocols. Variants with tolerated substitutions at residue 19 were identified by protein expression (see below). C151S active site substitutions were introduced into these variants as described above, to assess the differences in catalytic activity. Generated variants and their amino acid sequences are shown in Table 2. Exemplary cDNA sequences are shown for the wild type NIa (SEQ ID NO: 40) and for the following NIa variants: C151S (SEQ ID NO: 41), C19V/C110S/C181S/C211S (SEQ ID NO: 42), C19V/C110S/C151S/C181S/C211S (SEQ ID NO: 43), His6-WT (SEQ ID NO: 44), WT-His6 (SEQ ID NO: 45), C151S-His6 (SEQ ID NO: 46), C19V/C110S/C181S/C211S-His6 (SEQ ID NO: 47), and C19V/C110S/C151S/C181S/C211S-His6 (SEQ ID NO: 48).

TABLE 1

| Oligo | Sequence | SEQ ID NO: |
|---|---|---|
| PVAH6-5' | CTAACCATGGGCTCTACCTCTATGTTCCGTGGTGTTCGTGACTACAA | 49 |
| PVAH6-3' | GTTACTCGAGTTATTAATGGTGATGGTGATGGTGGGTAACCAGTTTAACGG | 50 |
| C151S-5' | CTACCAAAGACGGTCAGAGCGGTTCTCCGATCGTTTC | 51 |
| C151S-3' | GAAACGATCGGAGAACCGCTCTGACCGTCTTTGGTAG | 52 |
| C151A-5' | CTCTACCAAAGAAGGTCACGCCGGTTCTCCGATCGTTTC | 53 |
| C151A-3' | GAAACGATCGGAGAACCGGCGTGACCTTCTTTGGTAGAG | 54 |
| C19S-5' | CCCGATCTCTTCTGTTATCAGCCAGCTGGAAAACGAATCTGAAGG | 55 |
| C19S-3' | CCTTCAGATTCGTTTTCCAGCTGGCTGATAACAGAAGAGATCGGG | 56 |
| C110S-5' | CGACCCACTCTGAAAAAGTTAGCCTGATCCTGACCAACTTCCAG | 57 |
| C110S-3' | CTGGAAGTTGGTCAGGATCAGGCTAACTTTTTCAGAGTGGGTCG | 58 |
| C181S-5' | CACCTCTAACTACTTCGCGAGCTTCCCGAAAGGTTTCACCG | 59 |
| C181S-3' | CGGTGAAACCTTTCGGGAAGCTCGCGAAGTAGTTAGAGGTG | 60 |
| C211S-5' | CAACGCGTCTAACGTTAGCTGGGGTTCTTTCCACCTG | 61 |
| C211S-3' | CAGGTGGAAAGAACCCCAGCTAACGTTAGACGCGTTG | 62 |
| C19NNK-5' | ACCCGATCTCTTCTGTTATCNNKCAGCTGGAAAACGAATCTGAAG | 63 |
| C19NNK-3' | CTTCAGATTCGTTTTCCAGCTGMNNGATAACAGAAGAGATCGGGT | 64 |

TABLE 2

| NIa variant | SEQ ID NO: | DNA |
|---|---|---|
| WT | 1 | 40 |
| C151S | 2 | 41 |
| C110S | 3 | |
| C181S | 4 | |
| C211S | 5 | |
| C19S/C110S/C181S | 6 | |
| C19S/C110S/C211S | 7 | |
| C19S/C181S/C211S | 8 | |
| C19S/C110S/C181S/C211S | 9 | |
| C110S/C181S | 10 | |
| C110S/C211S | 11 | |
| C19A/C110S/C181S/C211S | 12 | |
| C110S/C181S/C211S | 13 | |
| C19D/C110S/C181S/C211S | 14 | |
| C19E/C110S/C181S/C211S | 15 | |
| C19F/C110S/C181S/C211S | 16 | |
| C110S/C181S/C211S | 17 | |
| C19H/C110S/C181S/C211S | 18 | |

TABLE 2-continued

| NIa variant | SEQ ID NO: | DNA |
|---|---|---|
| C19I/C110S/C181S/C211S | 19 | |
| C19K/C110S/C181S/C211S | 20 | |
| C19L/C110S/C181S/C211S | 21 | |
| C19M/C110S/C181S/C211S | 22 | |
| C19N/C110S/C181S/C211S | 23 | |
| C19P/C110S/C181S/C211S | 24 | |
| C19Q/C110S/C181S/C211S | 25 | |
| C19R/C110S/C181S/C211S | 26 | |
| C19T/C110S/C181S/C211S | 27 | |
| C19V/C110S/C181S/C211S | 38* | 42 |
| C19W/C110S/C181S/C211S | 29 | |
| C19Y/C110S/C181S/C211S | 30 | |
| C110S/C151S/C181S/C211S | 31 | |
| C181S/C211S | 32 | |
| C19V/C110S/C151S/C181S/C211S | 33 | 43 |
| C151A | 34 | |
| His6-WT | 35 | 44 |
| WT-His6 | 36 | 45 |
| C151S-His6 | 37 | 46 |
| C19V/C110S/C181S/C211S-His6 | 38 | 47 |
| C19V/C110S/C151S/C181S/C211S-His6 | 39 | 48 |

*NIa variant has an amino acid sequence of residues 1-233 of SEQ ID NO: 38

Protein Expression

Plasmids encoding cDNAs for the NIa protease variants in Table 1 were transformed in BL21 cells and single colonies from the transformants cultured in LB media with 100 μg/ml kanamycin at +37° C. overnight. Induction took place when the cultures reached an OD600 of 0.6-0.8 with 1 mM IPTG, or by culturing the cells in TB auto-induction media (Overnight Express Autoinduction Media, EMD Biosciences, Gibbstown, N.J.). The cells were further cultured overnight at 25° C. or 18° C., centrifuged and stored at −80° C. All NIa protease variants with a wild-type C19 residue expressed very well in all surface sulfhydryl change combinations explored (Table 3).

For the NNK library, the constructs were screened for soluble protein expression in TB auto induction media, as described above. A Western blot was run to analyze the expression of the NNK variants.

order to evaluate the effect of oxidizing environment to protein expression, stability, and activity. Only under reducing conditions does the C151A variant with 4 free surface sulfhydryls collapse to a predominantly single, monomeric species. However, the proteases with all surface sulfhydryls changes behave as monomeric proteins in the complete absence of reducing agent. This suggests that these changes provide a clear physical benefit while retaining catalytic activity (see below).

TABLE 3

| Variant | Substitutions | | | | | Plasmid Number | Expression | Activity |
|---|---|---|---|---|---|---|---|---|
| | C19 | C110 | C181 | C211 | C151 | | | |
| His$_6$-WT | | | | | | pDR1706 | + | + |
| WT | | | | | | pDR2090 | + | + |
| C151S | | | | | S | pDR2092 | + | + |
| C151A | | | | | A | pDR2091 | + | |
| C110S | | S | | | | pDR3385 | + | |
| C181S | | | S | | | pDR3388 | + | |
| C211S | | | | S | | pDR3390 | + | |
| C19S/C110S/C181S | S | S | S | | | pDR3384 | − | |
| C19S/C110S/C211S | S | S | | S | | pDR3383 | − | |
| C19S/C181S/C211S | S | | S | S | | pDR3382 | − | |
| C19S/C110S/C181S/C211S | S | S | S | S | | pDR2371 | − | |
| C110S/C181S | | S | S | | | pDR3386 | + | |
| C110S/C211S | | S | | | | pDR3387 | + | |
| C110S/C181S/C211S | | S | S | S | | pDR3202 | + | + |
| C110S/C151S/C181S/C211S | | S | S | S | S | pDR3467 | + | + |
| C181S/C211S | | | S | S | | pDR3389 | + | |
| C19V/C110S/C181S/C211S | V | S | S | S | | pDR3217 | + | + |
| C19V/C110S/C151S/C181S/C211S | V | S | S | S | S | pDR3466 | + | + |

Although several of the position 19 NNK variants were detectable at low levels (variants I, K, L, M, R, S, T, W, Y, F, G and H substitutions) (1-2% of the wild-type NIa), the variant C19V was expressed at significantly higher level than any other variant, and at a level equivalent to the wild type NIa. Based on the information, the following variants were selected for further studies: WT, C151S, C110S/C181S/ C211S, C110S/C151S/C181S/C211S, C19V/C110S/C181S/ C211S and C19V/C110S/C151S/C181S/C211S.

Protein Purification

Protein purification was done using standard methods in the presence of a reducing agent, 2 mM TCEP. Briefly, cell pellets were resuspended in Buffer A (20 mM tris-HCl, pH 7.5, 500 mM NaCl, 2 mM TCEP) supplemented with 0.1 U/ml benzonase and 0.3 mg/ml lysozyme, soincated on ice, filtered, and the cleared lysates were loaded onto a 5 ml HisTrap HP (GE Biosciences, Piscataway, N.J.) column pre-equilibrated with buffer A using an AKTA Explorer purification system (GE Lifesciences, Piscataway, N.J.). Proteins were eluted using an imidazole step gradient of 50-500 mM imidazole in buffer A. Fractions were analyzed by SDS-PAGE and the fractions containing the protein of interest were pooled and concentrated and filtered, followed by further purification by size exclusion chromatography (SEC). Concentrated and clarified samples were loaded directly onto a Superdex75 SEC matrix (GE Lifesciences, Piscataway, N.J.) pre-equilibrated with buffer A and separated isocratically at a flow rate of 1 ml/min. Fractions were analyzed by SDS-PAGE and the fractions containing protein were pooled and tested for enzymatic activity. All purified variants expressed well and were purified to over 95% purity.

Some of the variants (C151A, C19V/C110S/C181S/ C211S and C19V/C110S/C151S/C181S/C211S) were also purified in the absence of the reducing agent, 2 mM TCEP, in Substrate and Activity Determination A wild-card recognition sequence, EXVXXQX (SEQ ID NO: 74), was used to search the polyprotein sequence of PVA to determine a consensus recognition sequence for the NIa protease. This was done independently of published work identifying the processing junction points within the PVA polyprotein (Mertis et al., J. General Virol., 83:1211-1221, 2002). Published and potential recognition sequences, as well as the consensus sequence determined in this study listed in Table 4. Synthetic peptides corresponding to select recognition sequences were synthesized using solid-phase peptide chemistry (Anaspec, San Jose, Calif.) and tested for cleavage by the wild type NIa protease. Reactions were performed in 20 mM tris-HCl, pH 8.0, 150 mM NaCl and 1 mM dithiothreitol (DTT) containing 5 µM PVA NIa protease and 500 µM peptide and were analyzed by reverse-phase HPLC and LC-MS.

Enzyme activity was also determined for each variant using a fusion substrate protein containing the NIa protease consensus recognition sequence, ENVTFQG (SEQ ID NO:65). The consensus sequence was engineered into a fusion protein and used as a substrate to assess the enzymatic activity for all PVA NIa protease variants. Since the sequence contained a consensus site for N-linked glycosylation (NVT), another sequence was explored, EAVTFQG (SEQ ID NO: 66), with equal success. These fusion proteins contained an N-terminal poly-histidine tag to facilitate purification, the PNIa protease consensus recognition sequence, an S-tag for sensitive detection of proteolytic cleavage and a highly soluble "filler" protein to facilitate soluble expression of the fusion substrate protein. This cassette was generated by amplifying the region between the 3' end of the thrombin cleavage site and the XhoI site in pET41 (Novagen), adding the recognition sequence and NdeI cloning site in the 5' primer and inserting into the NdeI and XhoI restriction sites of pET28 (Novagen). The "filler" proteins could then be inserted into the multiple cloning site pulled over from pET41. Polypeptide sequence of the fusion proteins with the ENVTFQG (SEQ ID NO: 65) and the EAVTFQG (SEQ ID NO: 66) consensus recognition sequences are shown in SEQ ID NOs: 67 and 68, respectively.

As fusion substrate controls, analogous constructs were generated with both TEV (Dougherty et al., Virology, 171: 356-364, 1989) and TVMV NIa protease recognition sequences (Nallamsetty et al., Protein Expr. and Purific. 38:108-115, 2004) (Table 4). Analogous to human rhinovirus 3C (HRV3C) recognition sequence, a fusion protein with a P2' proline was also generated for the consensus sequence and tested as a substrate (Table 4). All recognition sequences were inserted into the fusion substrate protein, described above, including the published recognition sequences for TEV and TVMV proteases listed. Reactions were performed in 20 mM Tris-HCl, pH 8.0, 150 mM NaCl and 1 mM DTT and allowed to run overnight at 37° C.

Although it has been shown that the substrate specificity of 3C-like proteases is very high (Tozer et al., The FEBS J. 272:514-523, 2004), NIa wild type protease was able to cleave the fusion substrate with the TVMV NIa protease recognition sequence, although at a much lower rate than the PVA NIa protease consensus sequence. However, the NIa wild type protease was unable to cleave either the TEV NIa protease recognition sequence or the PVA NIa protease consensus sequence with a P2' proline residue in this format, the latter suggesting some level of P2' specificity (Table 4).

quencher substrate peptide 4-(4-dimethylaminophenylazo) benzoyl (DABCYL)—YGENVTFQGSK-5-[(2-aminoethyl) amino]naphthalene-1-sulfonic acid (EDANS) (SEQ ID NO: 73) (Anaspec, San Jose, Calif.). Kinetic measurements were performed on a Spectramax M2 microplate reader (Molecular Devices) using an excitation wavelength of 340 nm and emission wavelength of 490 nm. The reactions were performed in 50 mM Tris-HCl, pH 8.0, 150 mM NaCl, 1 mM EDTA, 1 mM DTT with 2 mM enzyme and 0.1-300 M substrate and followed for 30 minutes at 37° C. Enzyme concentrations were determined from the calculated theoretical extinction coefficient. Initial velocities were determined for each and are shown in Table 5.

TABLE 5

| Variant | Plasmid Number | DTT | $V_{max}$ (RFU/min) | $K_m$ (uM) | Relative $K_{cat}/K_m$ |
|---|---|---|---|---|---|
| WT | pDR2090 | + | 78466 | 177.6 | 100 |
| C151S | pDR2092 | + | 3236 | 164.9 | 4.3 |
| C110S/C181S/C211S | pDR3202 | + | 51110 | 251.5 | 45.9 |
| C110S/C151S/C181S/C211S | pDR3467 | + | 2346 | 71.8 | 7.6 |
| C19V/C110S/C181S/C211S | pDR3217 | + | 75184 | 275.4 | 59.5 |
| C19V/C110S/C151S/C181S/C211S | pDR3466 | + | 1888 | 39.6 | 10.8 |
| C19V/C110S/C181S/C211S | pDR3217 | − | 53847 | 175.4 | 69.1 |

TABLE 4

| Junction* | Recognition Sequence | SEQ ID NO: | Synthetic Peptide** | SEQ ID NO: | Cleaved by NIa |
|---|---|---|---|---|---|
| P3/6K1 | EVVLFQA^ | 75 | SEVVLFQASS | 70 | Yes |
| 6K1/CI | NTVQFQS | 76 | | | |
| CI/6K2 | EAVQFQS^ | 77 | | | |
| 6K2/VPg | GVVAFQG | 78 | | | |
| VPg/Pro | ESVEFES | 79 | | | |
| NIa/NIb | EAVYTQG^ | 80 | SEAVYTQGSS | 71 | Yes |
| NIb/cap | DMVYFQA | 81 | | | |
| NA | ENVTKQL^ | 82 | SENVTKQLSS | 87 | No |
| NA | EMVTNQS^ | 83 | SEMVTNQSSS | 88 | No |
| Consensus | ENVTFQG | 65 | SENVTFQGSS | 72 | Yes |
| | ENVTFQGP | 84 | | | No |
| TEV | ENLYGQGS | 85 | | | No |
| TVMV | ETVRFQGS | 86 | | | Yes |

*As determined in Mertis et. al., 2002.
^Sequences that met the EXVXXQX search criteria and from which the consensus sequence peptide was generated
*Synthetic peptide used in the assays The wild type NIa protease and variants C151S, C110S/C181S/C211S, C110S/C151S/C181S/C211S, C19V/C110S/C181S/C211S and C19V/C110S/C151S/C181S/C211S were screened for activity against the fusion substrate protein with the ENVTFQG (SEQ ID NO: 66) consensus recognition site. Reaction conditions were identical to those described above. Proteolytic cleavage of the substrate was monitored by SDS-PAGE. Each NIa protease with an active site cysteine residue (WT, C110S/C181S/C211S, C19V/C110S/C181S/C211S) cleaved the substrate to completion under these conditions. The NIa protease active site variants (C151S, C110S/C151S/C181S/C211S, C19V/C110S/C151S/C181S/C211S) also cleaved the substrate, albeit with less efficiency (1-5% of substrate cleaved) when compared to the wild type NIa (data not shown).

Enzyme Kinetics

Wild-type NIa protease and active site and surface cysteine variants were tested for activity against the fluorophore/

TABLE 5-continued

| Variant | Plasmid Number | DTT | $V_{max}$ (RFU/min) | $K_m$ (uM) | Relative $K_{cat}/K_m$ |
|---|---|---|---|---|---|
| C19V/C110S/C151S/C181S/C211S | pDR3466 | − | 1358 | 43.1 | 7.1 |

The substitutions to the surface exposed cysteine residues had a minor effect on catalytic activity of NIa protease, whereas substitutions at the active site cysteine (C151) reduced activity significantly. This can be explained by the inability of the substituted serine to donate its hydroxyl proton required for catalysis in the micro-environment within the active site, whereas deprotonation of cysteine readily occurs at physiological pH.

However, to determine whether having a reducing agent present during the purification process as well as during activity measurements impacted only molecules with an active site cysteine; two PVA NIa protease variants (C19V/C110S/C181S/C211S and C19V/C110S/C151S/C181S/C211S) were purified and assayed in the absence of reductant. The absence of reductant had little effect on the activity of either variant (Table 5). This suggests that the active site cysteine in these proteins may not be overly sensitive to an oxidizing environment and liability is predominantly due to the non-active site cysteine residues.

The invention claimed is:

1. An isolated polynucleotide encoding a polypeptide comprising the amino acid sequence of SEQ ID NO: 13 or the amino acid sequence of residues 1-233 of SEQ ID NO:38, wherein the encoded polypeptide has potato virus A (PVA) nuclear inclusion protein (NIa) protease activity and is more resistant to oxidation than the polypeptide of SEQ ID NO:1.

2. An isolated polynucleotide comprising the nucleotide sequence of SEQ ID NO: 42.

3. A vector comprising the isolated polynucleotide of claim 1.

4. A vector comprising the polynucleotide sequence of SEQ ID NO: 42 or 47.

5. An isolated host cell comprising the vector of claim 3 or 4.

6. A method for expressing a polypeptide comprising the steps of:

a. providing the host cell of claim 5; and b. culturing the host cell under conditions sufficient for the expression of at least one polypeptide, wherein the at least one polypeptide comprises the amino acid sequence of SEQ ID NO: 13 or the amino acid sequence of residues 1-233 of SEQ ID NO:38.

* * * * *

SEQUENCE LISTING

```
<160> NUMBER OF SEQ ID NOS: 88

<210> SEQ ID NO 1
<211> LENGTH: 233
<212> TYPE: PRT
<213> ORGANISM: Potato Virus
<220> FEATURE:
<223> OTHER INFORMATION: NIa protease

<400> SEQUENCE: 1

Ser Thr Ser Met Phe Arg Gly Val Arg Asp Tyr Asn Pro Ile Ser Ser
1               5                   10                  15

Val Ile Cys Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

Val Arg Asn Asn Gly Ser Leu Thr Val Arg Ser Gln Met Gly Val Phe
    50                  55                  60

Lys Val Asn Ser Thr Val Thr Leu Gln Met Arg Pro Val Glu Gly Arg
65                  70                  75                  80

Asp Val Leu Ile Ile Lys Met Pro Lys Asp Phe Pro Pro Phe Pro Gln
                85                  90                  95

Arg Leu Lys Phe Arg Gln Pro Thr His Ser Glu Lys Val Cys Leu Ile
            100                 105                 110

Leu Thr Asn Phe Gln Gln Lys Ser Ser Ser Met Val Ser Glu Thr
        115                 120                 125

Ser His Ile Ile Pro Lys Glu Asn Thr Tyr Phe Trp Lys His Trp Ile
    130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Cys Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Cys Trp Gly Ser Phe His Leu Gln Asp Ser Lys Pro Thr Lys
    210                 215                 220

Glu Phe Lys Thr Val Lys Leu Val Thr
225                 230

<210> SEQ ID NO 2
<211> LENGTH: 233
<212> TYPE: PRT
<213> ORGANISM: Artificial Sequence
<220> FEATURE:
<223> OTHER INFORMATION: Potato virus C151S Mutant

<400> SEQUENCE: 2

Ser Thr Ser Met Phe Arg Gly Val Arg Asp Tyr Asn Pro Ile Ser Ser
1               5                   10                  15

Val Ile Cys Gln Leu Glu Asn Glu Ser Glu Gly Arg Thr Thr Gln Leu
            20                  25                  30
```

```
Phe Gly Leu Gly Phe Gly Pro Phe Ile Ile Thr Asn Gln His Leu Phe
            35                  40                  45

Val Arg Asn Asn Gly Ser Leu Thr Val Arg Ser Gln Met Gly Val Phe
 50                  55                  60

Lys Val Asn Ser Thr Val Thr Leu Gln Met Arg Pro Val Glu Gly Arg
 65                  70                  75                  80

Asp Val Leu Ile Ile Lys Met Pro Lys Asp Phe Pro Pro Phe Pro Gln
                 85                  90                  95

Arg Leu Lys Phe Arg Gln Pro Thr His Ser Glu Lys Val Cys Leu Ile
                100                 105                 110

Leu Thr Asn Phe Gln Gln Lys Ser Ser Ser Met Val Ser Glu Thr
            115                 120                 125

Ser His Ile Ile Pro Lys Glu Asn Thr Tyr Phe Trp Lys His Trp Ile
130                 135                 140

Ser Thr Lys Glu Gly His Ser Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Cys Phe Pro Lys Gly Phe Thr Glu Thr Tyr Leu Ala
                180                 185                 190

Thr Glu Ser Ala His Glu Trp Val Lys Gly Trp Lys Phe Asn Ala Ser
            195                 200                 205

Asn Val Cys Trp Gly Ser Phe His Leu Gln Asp Ser Lys Pro Thr Lys
            210                 215                 220

Glu Phe Lys Thr Val Lys Leu Val Thr
225                 230

<210> SEQ ID NO 3
<211> LENGTH: 233
<212> TYPE: PRT
<213> ORGANISM: Artificial Sequence
<220> FEATURE:
<223> OTHER INFORMATION: Potato Virus C110S Mutant

<400> SEQUENCE: 3

Ser Thr Ser Met Phe Arg Gly Val Arg Asp Tyr Asn Pro Ile Ser Ser
 1               5                  10                  15

Val Ile Cys Gln Leu Glu Asn Glu Ser Glu Gly Arg Thr Thr Gln Leu
                20                  25                  30

Phe Gly Leu Gly Phe Gly Pro Phe Ile Ile Thr Asn Gln His Leu Phe
            35                  40                  45

Val Arg Asn Asn Gly Ser Leu Thr Val Arg Ser Gln Met Gly Val Phe
 50                  55                  60

Lys Val Asn Ser Thr Val Thr Leu Gln Met Arg Pro Val Glu Gly Arg
 65                  70                  75                  80

Asp Val Leu Ile Ile Lys Met Pro Lys Asp Phe Pro Pro Phe Pro Gln
                 85                  90                  95

Arg Leu Lys Phe Arg Gln Pro Thr His Ser Glu Lys Val Ser Leu Ile
                100                 105                 110

Leu Thr Asn Phe Gln Gln Lys Ser Ser Ser Met Val Ser Glu Thr
            115                 120                 125

Ser His Ile Ile Pro Lys Glu Asn Thr Tyr Phe Trp Lys His Trp Ile
130                 135                 140

Ser Thr Lys Glu Gly His Cys Gly Ser Pro Ile Val Ser Thr Thr Asp
145                 150                 155                 160
```

```
Gly Ala Ile Leu Gly Ile His Ser Leu Ser Asn Met Thr Asn Thr Ser
                165                 170                 175

Asn Tyr Phe Ala Cys Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Cys Trp Gly Ser Phe His Leu Gln Asp Ser Lys Pro Thr Lys
    210                 215                 220

Glu Phe Lys Thr Val Lys Leu Val Thr
225                 230
```

<210> SEQ ID NO 4
<211> LENGTH: 233
<212> TYPE: PRT
<213> ORGANISM: Artificial Sequence
<220> FEATURE:
<223> OTHER INFORMATION: Potato Virus C181S Mutant

<400> SEQUENCE: 4

```
Ser Thr Ser Met Phe Arg Gly Val Arg Asp Tyr Asn Pro Ile Ser Ser
1               5                   10                  15

Val Ile Cys Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

Val Arg Asn Asn Gly Ser Leu Thr Val Arg Ser Gln Met Gly Val Phe
    50                  55                  60

Lys Val Asn Ser Thr Val Thr Leu Gln Met Arg Pro Val Glu Gly Arg
65                  70                  75                  80

Asp Val Leu Ile Ile Lys Met Pro Lys Asp Phe Pro Pro Phe Pro Gln
                85                  90                  95

Arg Leu Lys Phe Arg Gln Pro Thr His Ser Glu Lys Val Cys Leu Ile
            100                 105                 110

Leu Thr Asn Phe Gln Gln Lys Ser Ser Ser Met Val Ser Glu Thr
        115                 120                 125

Ser His Ile Ile Pro Lys Glu Asn Thr Tyr Phe Trp Lys His Trp Ile
    130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Ser Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Cys Trp Gly Ser Phe His Leu Gln Asp Ser Lys Pro Thr Lys
    210                 215                 220

Glu Phe Lys Thr Val Lys Leu Val Thr
225                 230
```

<210> SEQ ID NO 5
<211> LENGTH: 233
<212> TYPE: PRT
<213> ORGANISM: Artificial Sequence
<220> FEATURE:
<223> OTHER INFORMATION: Potato Virus C211S Mutant

<400> SEQUENCE: 5

```
Ser Thr Ser Met Phe Arg Gly Val Arg Asp Tyr Asn Pro Ile Ser Ser
1               5                   10                  15

Val Ile Cys Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
            35                  40                  45

Val Arg Asn Asn Gly Ser Leu Thr Val Arg Ser Gln Met Gly Val Phe
50                  55                  60

Lys Val Asn Ser Thr Val Thr Leu Gln Met Arg Pro Val Glu Gly Arg
65                  70                  75                  80

Asp Val Leu Ile Ile Lys Met Pro Lys Asp Phe Pro Pro Phe Pro Gln
                85                  90                  95

Arg Leu Lys Phe Arg Gln Pro Thr His Ser Glu Lys Val Cys Leu Ile
                100                 105                 110

Leu Thr Asn Phe Gln Gln Lys Ser Ser Ser Met Val Ser Glu Thr
                115                 120                 125

Ser His Ile Ile Pro Lys Glu Asn Thr Tyr Phe Trp Lys His Trp Ile
        130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Cys Phe Pro Lys Gly Phe Thr Glu Thr Tyr Leu Ala
                180                 185                 190

Thr Glu Ser Ala His Glu Trp Val Lys Gly Trp Lys Phe Asn Ala Ser
                195                 200                 205

Asn Val Ser Trp Gly Ser Phe His Leu Gln Asp Ser Lys Pro Thr Lys
        210                 215                 220

Glu Phe Lys Thr Val Lys Leu Val Thr
225                 230
```

<210> SEQ ID NO 6
<211> LENGTH: 233
<212> TYPE: PRT
<213> ORGANISM: Artificial Sequence
<220> FEATURE:
<223> OTHER INFORMATION: Potato Virus C19S/C110S/C181S Mutant

<400> SEQUENCE: 6

```
Ser Thr Ser Met Phe Arg Gly Val Arg Asp Tyr Asn Pro Ile Ser Ser
1               5                   10                  15

Val Ile Ser Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
            35                  40                  45

Val Arg Asn Asn Gly Ser Leu Thr Val Arg Ser Gln Met Gly Val Phe
50                  55                  60

Lys Val Asn Ser Thr Val Thr Leu Gln Met Arg Pro Val Glu Gly Arg
65                  70                  75                  80

Asp Val Leu Ile Ile Lys Met Pro Lys Asp Phe Pro Pro Phe Pro Gln
                85                  90                  95

Arg Leu Lys Phe Arg Gln Pro Thr His Ser Glu Lys Val Ser Leu Ile
                100                 105                 110

Leu Thr Asn Phe Gln Gln Lys Ser Ser Ser Met Val Ser Glu Thr
                115                 120                 125
```

```
Ser His Ile Ile Pro Lys Glu Asn Thr Tyr Phe Trp Lys His Trp Ile
        130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Ser Phe Pro Lys Gly Phe Thr Glu Thr Tyr Leu Ala
                180                 185                 190

Thr Glu Ser Ala His Glu Trp Val Lys Gly Trp Lys Phe Asn Ala Ser
        195                 200                 205

Asn Val Cys Trp Gly Ser Phe His Leu Gln Asp Ser Lys Pro Thr Lys
        210                 215                 220

Glu Phe Lys Thr Val Lys Leu Val Thr
225                 230
```

<210> SEQ ID NO 7
<211> LENGTH: 233
<212> TYPE: PRT
<213> ORGANISM: Artificial Sequence
<220> FEATURE:
<223> OTHER INFORMATION: Potato Virus C19S/C110S/C211S Mutant

<400> SEQUENCE: 7

```
Ser Thr Ser Met Phe Arg Gly Val Arg Asp Tyr Asn Pro Ile Ser Ser
  1               5                  10                  15

Val Ile Ser Gln Leu Glu Asn Glu Ser Glu Gly Arg Thr Thr Gln Leu
                 20                  25                  30

Phe Gly Leu Gly Phe Gly Pro Phe Ile Ile Thr Asn Gln His Leu Phe
             35                  40                  45

Val Arg Asn Asn Gly Ser Leu Thr Val Arg Ser Gln Met Gly Val Phe
 50                  55                  60

Lys Val Asn Ser Thr Val Thr Leu Gln Met Arg Pro Val Glu Gly Arg
 65                  70                  75                  80

Asp Val Leu Ile Ile Lys Met Pro Lys Asp Phe Pro Pro Phe Pro Gln
                 85                  90                  95

Arg Leu Lys Phe Arg Gln Pro Thr His Ser Glu Lys Val Ser Leu Ile
            100                 105                 110

Leu Thr Asn Phe Gln Gln Lys Ser Ser Ser Met Val Ser Glu Thr
            115                 120                 125

Ser His Ile Ile Pro Lys Glu Asn Thr Tyr Phe Trp Lys His Trp Ile
        130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Cys Phe Pro Lys Gly Phe Thr Glu Thr Tyr Leu Ala
                180                 185                 190

Thr Glu Ser Ala His Glu Trp Val Lys Gly Trp Lys Phe Asn Ala Ser
        195                 200                 205

Asn Val Ser Trp Gly Ser Phe His Leu Gln Asp Ser Lys Pro Thr Lys
        210                 215                 220

Glu Phe Lys Thr Val Lys Leu Val Thr
225                 230
```

<210> SEQ ID NO 8

<211> LENGTH: 233
<212> TYPE: PRT
<213> ORGANISM: Artificial Sequence
<220> FEATURE:
<223> OTHER INFORMATION: PVA C19S/C181S/C211S mutant

<400> SEQUENCE: 8

```
Ser Thr Ser Met Phe Arg Gly Val Arg Asp Tyr Asn Pro Ile Ser Ser
 1               5                  10                  15

Val Ile Ser Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

Val Arg Asn Asn Gly Ser Leu Thr Val Arg Ser Gln Met Gly Val Phe
    50                  55                  60

Lys Val Asn Ser Thr Val Thr Leu Gln Met Arg Pro Val Glu Gly Arg
 65                  70                  75                  80

Asp Val Leu Ile Ile Lys Met Pro Lys Asp Phe Pro Pro Phe Pro Gln
                 85                  90                  95

Arg Leu Lys Phe Arg Gln Pro Thr His Ser Glu Lys Val Cys Leu Ile
            100                 105                 110

Leu Thr Asn Phe Gln Gln Lys Ser Ser Ser Met Val Ser Glu Thr
        115                 120                 125

Ser His Ile Ile Pro Lys Glu Asn Thr Tyr Phe Trp Lys His Trp Ile
    130                 135                 140

Ser Thr Lys Glu Gly His Cys Gly Ser Pro Ile Val Ser Thr Asp
145                 150                 155                 160

Gly Ala Ile Leu Gly Ile His Ser Leu Ser Asn Met Thr Asn Thr Ser
                165                 170                 175

Asn Tyr Phe Ala Ser Phe Pro Lys Gly Phe Thr Glu Tyr Leu Ala
            180                 185                 190

Thr Glu Ser Ala His Glu Trp Val Lys Gly Trp Lys Phe Asn Ala Ser
        195                 200                 205

Asn Val Ser Trp Gly Ser Phe His Leu Gln Asp Ser Lys Pro Thr Lys
    210                 215                 220

Glu Phe Lys Thr Val Lys Leu Val Thr
225                 230
```

<210> SEQ ID NO 9
<211> LENGTH: 233
<212> TYPE: PRT
<213> ORGANISM: Artificial Sequence
<220> FEATURE:
<223> OTHER INFORMATION: PVA Protease C19S/C110S/C181S/C211S mutant

<400> SEQUENCE: 9

```
Ser Thr Ser Met Phe Arg Gly Val Arg Asp Tyr Asn Pro Ile Ser Ser
 1               5                  10                  15

Val Ile Ser Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

Val Arg Asn Asn Gly Ser Leu Thr Val Arg Ser Gln Met Gly Val Phe
    50                  55                  60

Lys Val Asn Ser Thr Val Thr Leu Gln Met Arg Pro Val Glu Gly Arg
 65                  70                  75                  80

Asp Val Leu Ile Ile Lys Met Pro Lys Asp Phe Pro Pro Phe Pro Gln
```

```
                 85                  90                  95
Arg Leu Lys Phe Arg Gln Pro Thr His Ser Glu Lys Val Ser Leu Ile
                100                 105                 110
Leu Thr Asn Phe Gln Gln Lys Ser Ser Ser Met Val Ser Glu Thr
            115                 120                 125
Ser His Ile Ile Pro Lys Glu Asn Thr Tyr Phe Trp Lys His Trp Ile
130                 135                 140
Ser Thr Lys Glu Gly His Cys Gly Ser Pro Ile Val Ser Thr Thr Asp
145                 150                 155                 160
Gly Ala Ile Leu Gly Ile His Ser Leu Ser Asn Met Thr Asn Thr Ser
                165                 170                 175
Asn Tyr Phe Ala Ser Phe Pro Lys Gly Phe Thr Glu Thr Tyr Leu Ala
                180                 185                 190
Thr Glu Ser Ala His Glu Trp Val Lys Gly Trp Lys Phe Asn Ala Ser
                195                 200                 205
Asn Val Ser Trp Gly Ser Phe His Leu Gln Asp Ser Lys Pro Thr Lys
                210                 215                 220
Glu Phe Lys Thr Val Lys Leu Val Thr
225                 230
```

<210> SEQ ID NO 10
<211> LENGTH: 233
<212> TYPE: PRT
<213> ORGANISM: Artificial Sequence
<220> FEATURE:
<223> OTHER INFORMATION: PVA Protease C110S/C181S mutant

<400> SEQUENCE: 10

```
Ser Thr Ser Met Phe Arg Gly Val Arg Asp Tyr Asn Pro Ile Ser Ser
1               5                   10                  15
Val Ile Cys Gln Leu Glu Asn Glu Ser Glu Gly Arg Thr Thr Gln Leu
                20                  25                  30
Phe Gly Leu Gly Phe Gly Pro Phe Ile Ile Thr Asn Gln His Leu Phe
            35                  40                  45
Val Arg Asn Asn Gly Ser Leu Thr Val Arg Ser Gln Met Gly Val Phe
50                  55                  60
Lys Val Asn Ser Thr Val Thr Leu Gln Met Arg Pro Val Glu Gly Arg
65                  70                  75                  80
Asp Val Leu Ile Ile Lys Met Pro Lys Asp Phe Pro Phe Pro Pro Gln
                85                  90                  95
Arg Leu Lys Phe Arg Gln Pro Thr His Ser Glu Lys Val Ser Leu Ile
                100                 105                 110
Leu Thr Asn Phe Gln Gln Lys Ser Ser Ser Met Val Ser Glu Thr
            115                 120                 125
Ser His Ile Ile Pro Lys Glu Asn Thr Tyr Phe Trp Lys His Trp Ile
130                 135                 140
Ser Thr Lys Glu Gly His Cys Gly Ser Pro Ile Val Ser Thr Thr Asp
145                 150                 155                 160
Gly Ala Ile Leu Gly Ile His Ser Leu Ser Asn Met Thr Asn Thr Ser
                165                 170                 175
Asn Tyr Phe Ala Ser Phe Pro Lys Gly Phe Thr Glu Thr Tyr Leu Ala
                180                 185                 190
Thr Glu Ser Ala His Glu Trp Val Lys Gly Trp Lys Phe Asn Ala Ser
                195                 200                 205
Asn Val Cys Trp Gly Ser Phe His Leu Gln Asp Ser Lys Pro Thr Lys
```

Glu Phe Lys Thr Val Lys Leu Val Thr
225                 230

<210> SEQ ID NO 11
<211> LENGTH: 233
<212> TYPE: PRT
<213> ORGANISM: Artificial Sequence
<220> FEATURE:
<223> OTHER INFORMATION: PVA Protease C110S/C211S mutant

<400> SEQUENCE: 11

Ser Thr Ser Met Phe Arg Gly Val Arg Asp Tyr Asn Pro Ile Ser Ser
1               5                   10                  15

Val Ile Cys Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

Val Arg Asn Asn Gly Ser Leu Thr Val Arg Ser Gln Met Gly Val Phe
    50                  55                  60

Lys Val Asn Ser Thr Val Thr Leu Gln Met Arg Pro Val Glu Gly Arg
65                  70                  75                  80

Asp Val Leu Ile Ile Lys Met Pro Lys Asp Phe Pro Pro Phe Pro Gln
                85                  90                  95

Arg Leu Lys Phe Arg Gln Pro Thr His Ser Glu Lys Val Ser Leu Ile
            100                 105                 110

Leu Thr Asn Phe Gln Gln Lys Ser Ser Ser Met Val Ser Glu Thr
        115                 120                 125

Ser His Ile Ile Pro Lys Glu Asn Thr Tyr Phe Trp Lys His Trp Ile
    130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Cys Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Ser Trp Gly Ser Phe His Leu Gln Asp Ser Lys Pro Thr Lys
    210                 215                 220

Glu Phe Lys Thr Val Lys Leu Val Thr
225                 230

<210> SEQ ID NO 12
<211> LENGTH: 233
<212> TYPE: PRT
<213> ORGANISM: Artificial Sequence
<220> FEATURE:
<223> OTHER INFORMATION: PVA Protease C19A/C110S/C181S/C211S mutant

<400> SEQUENCE: 12

Ser Thr Ser Met Phe Arg Gly Val Arg Asp Tyr Asn Pro Ile Ser Ser
1               5                   10                  15

Val Ile Ala Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

```
Val Arg Asn Asn Gly Ser Leu Thr Val Arg Ser Gln Met Gly Val Phe
 50                  55                  60

Lys Val Asn Ser Thr Val Thr Leu Gln Met Arg Pro Val Glu Gly Arg
 65                  70                  75                  80

Asp Val Leu Ile Ile Lys Met Pro Lys Asp Phe Pro Pro Phe Pro Gln
                 85                  90                  95

Arg Leu Lys Phe Arg Gln Pro Thr His Ser Glu Lys Val Ser Leu Ile
                100                 105                 110

Leu Thr Asn Phe Gln Gln Lys Ser Ser Ser Met Val Ser Glu Thr
                115                 120                 125

Ser His Ile Ile Pro Lys Glu Asn Thr Tyr Phe Trp Lys His Trp Ile
130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Ser Phe Pro Lys Gly Phe Thr Glu Thr Tyr Leu Ala
                180                 185                 190

Thr Glu Ser Ala His Glu Trp Val Lys Gly Trp Lys Phe Asn Ala Ser
                195                 200                 205

Asn Val Ser Trp Gly Ser Phe His Leu Gln Asp Ser Lys Pro Thr Lys
210                 215                 220

Glu Phe Lys Thr Val Lys Leu Val Thr
225                 230

<210> SEQ ID NO 13
<211> LENGTH: 233
<212> TYPE: PRT
<213> ORGANISM: Artificial Sequence
<220> FEATURE:
<223> OTHER INFORMATION: PVA Protease C110S/C181S/C211S mutant

<400> SEQUENCE: 13

Ser Thr Ser Met Phe Arg Gly Val Arg Asp Tyr Asn Pro Ile Ser Ser
 1                   5                  10                  15

Val Ile Cys Gln Leu Glu Asn Glu Ser Glu Gly Arg Thr Arg Gln Leu
                 20                  25                  30

Phe Gly Leu Gly Phe Gly Pro Phe Ile Ile Thr Asn Gln His Leu Phe
                 35                  40                  45

Val Arg Asn Asn Gly Ser Leu Thr Val Arg Ser Gln Met Gly Val Phe
 50                  55                  60

Lys Val Asn Ser Thr Val Thr Leu Gln Met Arg Pro Val Glu Gly Arg
 65                  70                  75                  80

Asp Val Leu Ile Ile Lys Met Pro Lys Asp Phe Pro Pro Phe Pro Gln
                 85                  90                  95

Arg Leu Lys Phe Arg Gln Pro Thr His Ser Glu Lys Val Ser Leu Ile
                100                 105                 110

Leu Thr Asn Phe Gln Gln Lys Ser Ser Ser Met Val Ser Glu Thr
                115                 120                 125

Ser His Ile Ile Pro Lys Glu Asn Thr Tyr Phe Trp Lys His Trp Ile
130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175
```

```
Asn Tyr Phe Ala Ser Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Ser Trp Gly Ser Phe His Leu Gln Asp Ser Lys Pro Thr Lys
    210                 215                 220

Glu Phe Lys Thr Val Lys Leu Val Thr
225                 230

<210> SEQ ID NO 14
<211> LENGTH: 233
<212> TYPE: PRT
<213> ORGANISM: Artificial Sequence
<220> FEATURE:
<223> OTHER INFORMATION: PVA Protease C19D/C110S/C181S/C211S mutant

<400> SEQUENCE: 14

Ser Thr Ser Met Phe Arg Gly Val Arg Asp Tyr Asn Pro Ile Ser Ser
1               5                   10                  15

Val Ile Asp Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

Val Arg Asn Asn Gly Ser Leu Thr Val Arg Ser Gln Met Gly Val Phe
    50                  55                  60

Lys Val Asn Ser Thr Val Thr Leu Gln Met Arg Pro Val Glu Gly Arg
65                  70                  75                  80

Asp Val Leu Ile Ile Lys Met Pro Lys Asp Phe Pro Pro Phe Pro Gln
                85                  90                  95

Arg Leu Lys Phe Arg Gln Pro Thr His Ser Glu Lys Val Ser Leu Ile
            100                 105                 110

Leu Thr Asn Phe Gln Gln Lys Ser Ser Ser Met Val Ser Glu Thr
        115                 120                 125

Ser His Ile Ile Pro Lys Glu Asn Thr Tyr Phe Trp Lys His Trp Ile
    130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Ser Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Ser Trp Gly Ser Phe His Leu Gln Asp Ser Lys Pro Thr Lys
    210                 215                 220

Glu Phe Lys Thr Val Lys Leu Val Thr
225                 230

<210> SEQ ID NO 15
<211> LENGTH: 233
<212> TYPE: PRT
<213> ORGANISM: Artificial Sequence
<220> FEATURE:
<223> OTHER INFORMATION: PVA Protease C19E/C110S/C181S/C211S mutant

<400> SEQUENCE: 15

Ser Thr Ser Met Phe Arg Gly Val Arg Asp Tyr Asn Pro Ile Ser Ser
1               5                   10                  15
```

```
Val Ile Glu Gln Leu Glu Asn Glu Ser Glu Gly Arg Thr Thr Gln Leu
         20                  25                  30

Phe Gly Leu Gly Phe Gly Pro Phe Ile Ile Thr Asn Gln His Leu Phe
             35                  40                  45

Val Arg Asn Asn Gly Ser Leu Thr Val Arg Ser Gln Met Gly Val Phe
 50                  55                  60

Lys Val Asn Ser Thr Val Thr Leu Gln Met Arg Pro Val Glu Gly Arg
 65                  70                  75                  80

Asp Val Leu Ile Ile Lys Met Pro Lys Asp Phe Pro Pro Phe Pro Gln
                 85                  90                  95

Arg Leu Lys Phe Arg Gln Pro Thr His Ser Glu Lys Val Ser Leu Ile
                100                 105                 110

Leu Thr Asn Phe Gln Gln Lys Ser Ser Ser Met Val Ser Glu Thr
             115                 120                 125

Ser His Ile Ile Pro Lys Glu Asn Thr Tyr Phe Trp Lys His Trp Ile
130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Ser Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Ser Trp Gly Ser Phe His Leu Gln Asp Ser Lys Pro Thr Lys
    210                 215                 220

Glu Phe Lys Thr Val Lys Leu Val Thr
225                 230

<210> SEQ ID NO 16
<211> LENGTH: 235
<212> TYPE: PRT
<213> ORGANISM: Artificial Sequence
<220> FEATURE:
<223> OTHER INFORMATION: PVA Protease C19F/C110S/C181S/C211S

<400> SEQUENCE: 16

Met Gly Ser Thr Ser Met Phe Arg Gly Val Arg Asp Tyr Asn Pro Ile
 1               5                  10                  15

Ser Ser Val Ile Phe Gln Leu Glu Asn Glu Ser Glu Gly Arg Thr Thr
             20                  25                  30

Gln Leu Phe Gly Leu Gly Phe Gly Pro Phe Ile Ile Thr Asn Gln His
         35                  40                  45

Leu Phe Val Arg Asn Asn Gly Ser Leu Thr Val Arg Ser Gln Met Gly
     50                  55                  60

Val Phe Lys Val Asn Ser Thr Val Thr Leu Gln Met Arg Pro Val Glu
 65                  70                  75                  80

Gly Arg Asp Val Leu Ile Ile Lys Met Pro Lys Asp Phe Pro Pro Phe
                 85                  90                  95

Pro Gln Arg Leu Lys Phe Arg Gln Pro Thr His Ser Glu Lys Val Ser
                100                 105                 110

Leu Ile Leu Thr Asn Phe Gln Gln Lys Ser Ser Ser Met Val Ser
            115                 120                 125

Glu Thr Ser His Ile Ile Pro Lys Glu Asn Thr Tyr Phe Trp Lys His
130                 135                 140
```

Trp Ile Ser Thr Lys Glu Gly His Cys Gly Ser Pro Ile Val Ser Thr
145                 150                 155                 160

Thr Asp Gly Ala Ile Leu Gly Ile His Ser Leu Ser Asn Met Thr Asn
                165                 170                 175

Thr Ser Asn Tyr Phe Ala Ser Phe Pro Lys Gly Phe Thr Glu Thr Tyr
            180                 185                 190

Leu Ala Thr Glu Ser Ala His Glu Trp Val Lys Gly Trp Lys Phe Asn
        195                 200                 205

Ala Ser Asn Val Ser Trp Gly Ser Phe His Leu Gln Asp Ser Lys Pro
    210                 215                 220

Thr Lys Glu Phe Lys Thr Val Lys Leu Val Thr
225                 230                 235

<210> SEQ ID NO 17
<211> LENGTH: 233
<212> TYPE: PRT
<213> ORGANISM: Artificial Sequence
<220> FEATURE:
<223> OTHER INFORMATION: PVA Protease C19G/C110S/C181S/C211S mutant

<400> SEQUENCE: 17

Ser Thr Ser Met Phe Arg Gly Val Arg Asp Tyr Asn Pro Ile Ser Ser
1               5                   10                  15

Val Ile Gly Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

Val Arg Asn Asn Gly Ser Leu Thr Val Arg Ser Gln Met Gly Val Phe
    50                  55                  60

Lys Val Asn Ser Thr Val Thr Leu Gln Met Arg Pro Val Glu Gly Arg
65                  70                  75                  80

Asp Val Leu Ile Ile Lys Met Pro Lys Asp Phe Pro Pro Phe Pro Gln
                85                  90                  95

Arg Leu Lys Phe Arg Gln Pro Thr His Ser Glu Lys Val Ser Leu Ile
            100                 105                 110

Leu Thr Asn Phe Gln Gln Lys Ser Ser Ser Met Val Ser Glu Thr
        115                 120                 125

Ser His Ile Ile Pro Lys Glu Asn Thr Tyr Phe Trp Lys His Trp Ile
    130                 135                 140

Ser Thr Lys Glu Gly His Cys Gly Ser Pro Ile Val Ser Thr Asp
145                 150                 155                 160

Gly Ala Ile Leu Gly Ile His Ser Leu Ser Asn Met Thr Asn Thr Ser
                165                 170                 175

Asn Tyr Phe Ala Ser Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Ser Trp Gly Ser Phe His Leu Gln Asp Ser Lys Pro Thr Lys
    210                 215                 220

Glu Phe Lys Thr Val Lys Leu Val Thr
225                 230

<210> SEQ ID NO 18
<211> LENGTH: 233
<212> TYPE: PRT
<213> ORGANISM: Artificial Sequence -continued

```
<220> FEATURE:
<223> OTHER INFORMATION: PVA Protease C19H/C110S/C181S/C211S mutant

<400> SEQUENCE: 18

Ser Thr Ser Met Phe Arg Gly Val Arg Asp Tyr Asn Pro Ile Ser Ser
1               5                   10                  15

Val Ile His Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

Val Arg Asn Asn Gly Ser Leu Thr Val Arg Ser Gln Met Gly Val Phe
    50                  55                  60

Lys Val Asn Ser Thr Val Thr Leu Gln Met Arg Pro Val Glu Gly Arg
65                  70                  75                  80

Asp Val Leu Ile Ile Lys Met Pro Lys Asp Phe Pro Pro Phe Pro Gln
                85                  90                  95

Arg Leu Lys Phe Arg Gln Pro Thr His Ser Glu Lys Val Ser Leu Ile
            100                 105                 110

Leu Thr Asn Phe Gln Gln Lys Ser Ser Ser Met Val Ser Glu Thr
        115                 120                 125

Ser His Ile Ile Pro Lys Glu Asn Thr Tyr Phe Trp Lys His Trp Ile
    130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Ser Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Ser Trp Gly Ser Phe His Leu Gln Asp Ser Lys Pro Thr Lys
    210                 215                 220

Glu Phe Lys Thr Val Lys Leu Val Thr
225                 230

<210> SEQ ID NO 19
<211> LENGTH: 233
<212> TYPE: PRT
<213> ORGANISM: Artificial Sequence
<220> FEATURE:
<223> OTHER INFORMATION: PVA Protease C19I/C110S/C181S/C211S mutant

<400> SEQUENCE: 19

Ser Thr Ser Met Phe Arg Gly Val Arg Asp Tyr Asn Pro Ile Ser Ser
1               5                   10                  15

Val Ile Ile Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

Val Arg Asn Asn Gly Ser Leu Thr Val Arg Ser Gln Met Gly Val Phe
    50                  55                  60

Lys Val Asn Ser Thr Val Thr Leu Gln Met Arg Pro Val Glu Gly Arg
65                  70                  75                  80

Asp Val Leu Ile Ile Lys Met Pro Lys Asp Phe Pro Pro Phe Pro Gln
                85                  90                  95

Arg Leu Lys Phe Arg Gln Pro Thr His Ser Glu Lys Val Ser Leu Ile
```

```
                100                 105                 110
Leu Thr Asn Phe Gln Gln Lys Ser Ser Ser Met Val Ser Glu Thr
            115                 120                 125
Ser His Ile Ile Pro Lys Glu Asn Thr Tyr Phe Trp Lys His Trp Ile
130                 135                 140
Ser Thr Lys Glu Gly His Cys Gly Ser Pro Ile Val Ser Thr Thr Asp
145                 150                 155                 160
Gly Ala Ile Leu Gly Ile His Ser Leu Ser Asn Met Thr Asn Thr Ser
                165                 170                 175
Asn Tyr Phe Ala Ser Phe Pro Lys Gly Phe Thr Glu Thr Tyr Leu Ala
            180                 185                 190
Thr Glu Ser Ala His Glu Trp Val Lys Gly Trp Lys Phe Asn Ala Ser
            195                 200                 205
Asn Val Ser Trp Gly Ser Phe His Leu Gln Asp Ser Lys Pro Thr Lys
            210                 215                 220
Glu Phe Lys Thr Val Lys Leu Val Thr
225                 230
```

<210> SEQ ID NO 20
<211> LENGTH: 233
<212> TYPE: PRT
<213> ORGANISM: Artificial Sequence
<220> FEATURE:
<223> OTHER INFORMATION: PVA Protease C19K/C110S/C181S/C211S mutant

<400> SEQUENCE: 20

```
Ser Thr Ser Met Phe Arg Gly Val Arg Asp Tyr Asn Pro Ile Ser Ser
1               5                   10                  15
Val Ile Lys Gln Leu Glu Asn Glu Ser Glu Gly Arg Thr Thr Gln Leu
            20                  25                  30
Phe Gly Leu Gly Phe Gly Pro Phe Ile Ile Thr Asn Gln His Leu Phe
        35                  40                  45
Val Arg Asn Asn Gly Ser Leu Thr Val Arg Ser Gln Met Gly Val Phe
50                  55                  60
Lys Val Asn Ser Thr Val Thr Leu Gln Met Arg Pro Val Glu Gly Arg
65                  70                  75                  80
Asp Val Leu Ile Ile Lys Met Pro Lys Asp Phe Pro Pro Phe Pro Gln
                85                  90                  95
Arg Leu Lys Phe Arg Gln Pro Thr His Ser Glu Lys Val Ser Leu Ile
            100                 105                 110
Leu Thr Asn Phe Gln Gln Lys Ser Ser Ser Met Val Ser Glu Thr
            115                 120                 125
Ser His Ile Ile Pro Lys Glu Asn Thr Tyr Phe Trp Lys His Trp Ile
130                 135                 140
Ser Thr Lys Glu Gly His Cys Gly Ser Pro Ile Val Ser Thr Thr Asp
145                 150                 155                 160
Gly Ala Ile Leu Gly Ile His Ser Leu Ser Asn Met Thr Asn Thr Ser
                165                 170                 175
Asn Tyr Phe Ala Ser Phe Pro Lys Gly Phe Thr Glu Thr Tyr Leu Ala
            180                 185                 190
Thr Glu Ser Ala His Glu Trp Val Lys Gly Trp Lys Phe Asn Ala Ser
            195                 200                 205
Asn Val Ser Trp Gly Ser Phe His Leu Gln Asp Ser Lys Pro Thr Lys
            210                 215                 220
Glu Phe Lys Thr Val Lys Leu Val Thr
```

<210> SEQ ID NO 21
<211> LENGTH: 233
<212> TYPE: PRT
<213> ORGANISM: Artificial Sequence
<220> FEATURE:
<223> OTHER INFORMATION: PVA Protease C19L/C110S/C181S/C211S mutant

<400> SEQUENCE: 21

```
Ser Thr Ser Met Phe Arg Gly Val Arg Asp Tyr Asn Pro Ile Ser Ser
1               5                   10                  15

Val Ile Leu Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

Val Arg Asn Asn Gly Ser Leu Thr Val Arg Ser Gln Met Gly Val Phe
    50                  55                  60

Lys Val Asn Ser Thr Val Thr Leu Gln Met Arg Pro Val Glu Gly Arg
65                  70                  75                  80

Asp Val Leu Ile Ile Lys Met Pro Lys Asp Phe Pro Pro Phe Pro Gln
                85                  90                  95

Arg Leu Lys Phe Arg Gln Pro Thr His Ser Glu Lys Val Ser Leu Ile
            100                 105                 110

Leu Thr Asn Phe Gln Gln Lys Ser Ser Ser Met Val Ser Glu Thr
        115                 120                 125

Ser His Ile Ile Pro Lys Glu Asn Thr Tyr Phe Trp Lys His Trp Ile
    130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Ser Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Ser Trp Gly Ser Phe His Leu Gln Asp Ser Lys Pro Thr Lys
    210                 215                 220

Glu Phe Lys Thr Val Lys Leu Val Thr
225                 230
```

<210> SEQ ID NO 22
<211> LENGTH: 233
<212> TYPE: PRT
<213> ORGANISM: Artificial Sequence
<220> FEATURE:
<223> OTHER INFORMATION: PVA Protease C19M/C110S/C181S/C211S mutant

<400> SEQUENCE: 22

```
Ser Thr Ser Met Phe Arg Gly Val Arg Asp Tyr Asn Pro Ile Ser Ser
1               5                   10                  15

Val Ile Met Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

Val Arg Asn Asn Gly Ser Leu Thr Val Arg Ser Gln Met Gly Val Phe
    50                  55                  60
```

```
Lys Val Asn Ser Thr Val Thr Leu Gln Met Arg Pro Val Glu Gly Arg
 65                  70                  75                  80

Asp Val Leu Ile Ile Lys Met Pro Lys Asp Phe Pro Pro Phe Pro Gln
                 85                  90                  95

Arg Leu Lys Phe Arg Gln Pro Thr His Ser Glu Lys Val Ser Leu Ile
            100                 105                 110

Leu Thr Asn Phe Gln Gln Lys Ser Ser Ser Met Val Ser Glu Thr
        115                 120                 125

Ser His Ile Ile Pro Lys Glu Asn Thr Tyr Phe Trp Lys His Trp Ile
130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Ser Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
            195                 200                 205

Asn Val Ser Trp Gly Ser Phe His Leu Gln Asp Ser Lys Pro Thr Lys
210                 215                 220

Glu Phe Lys Thr Val Lys Leu Val Thr
225                 230

<210> SEQ ID NO 23
<211> LENGTH: 233
<212> TYPE: PRT
<213> ORGANISM: Artificial Sequence
<220> FEATURE:
<223> OTHER INFORMATION: PVA Protease C19N/C110S/C181S/C211S mutant

<400> SEQUENCE: 23

Ser Thr Ser Met Phe Arg Gly Val Arg Asp Tyr Asn Pro Ile Ser Ser
  1               5                  10                  15

Val Ile Asn Gln Leu Glu Asn Glu Ser Glu Gly Arg Thr Thr Gln Leu
             20                  25                  30

Phe Gly Leu Gly Phe Gly Pro Phe Ile Ile Thr Asn Gln His Leu Phe
         35                  40                  45

Val Arg Asn Asn Gly Ser Leu Thr Val Arg Ser Gln Met Gly Val Phe
     50                  55                  60

Lys Val Asn Ser Thr Val Thr Leu Gln Met Arg Pro Val Glu Gly Arg
 65                  70                  75                  80

Asp Val Leu Ile Ile Lys Met Pro Lys Asp Phe Pro Pro Phe Pro Gln
                 85                  90                  95

Arg Leu Lys Phe Arg Gln Pro Thr His Ser Glu Lys Val Ser Leu Ile
            100                 105                 110

Leu Thr Asn Phe Gln Gln Lys Ser Ser Ser Met Val Ser Glu Thr
        115                 120                 125

Ser His Ile Ile Pro Lys Glu Asn Thr Tyr Phe Trp Lys His Trp Ile
130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Ser Phe Pro Lys Gly Phe Thr Glu Thr Tyr Leu Ala
            180                 185                 190
```

```
Thr Glu Ser Ala His Glu Trp Val Lys Gly Trp Lys Phe Asn Ala Ser
            195                 200                 205

Asn Val Ser Trp Gly Ser Phe His Leu Gln Asp Ser Lys Pro Thr Lys
        210                 215                 220

Glu Phe Lys Thr Val Lys Leu Val Thr
225                 230
```

<210> SEQ ID NO 24
<211> LENGTH: 156
<212> TYPE: PRT
<213> ORGANISM: Artificial Sequence
<220> FEATURE:
<223> OTHER INFORMATION: PVA Protease C19P/C110S/C181S/C211S mutant

<400> SEQUENCE: 24

```
Glu Gly Arg Asp Val Leu Ile Ile Lys Met Pro Lys Asp Phe Pro Pro
1               5                   10                  15

Phe Pro Gln Arg Leu Lys Phe Arg Gln Pro Thr His Ser Glu Lys Val
            20                  25                  30

Ser Leu Ile Leu Thr Asn Phe Gln Gln Lys Ser Ser Ser Ser Met Val
        35                  40                  45

Ser Glu Thr Ser His Ile Ile Pro Lys Glu Asn Thr Tyr Phe Trp Lys
    50                  55                  60

His Trp Ile Ser Thr Lys Glu Gly His Cys Gly Ser Pro Ile Val Ser
65                  70                  75                  80

Thr Thr Asp Gly Ala Ile Leu Gly Ile His Ser Leu Ser Asn Met Thr
                85                  90                  95

Asn Thr Ser Asn Tyr Phe Ala Ser Phe Pro Lys Gly Phe Thr Glu Thr
            100                 105                 110

Tyr Leu Ala Thr Glu Ser Ala His Glu Trp Val Lys Gly Trp Lys Phe
        115                 120                 125

Asn Ala Ser Asn Val Ser Trp Gly Ser Phe His Leu Gln Asp Ser Lys
    130                 135                 140

Pro Thr Lys Glu Phe Lys Thr Val Lys Leu Val Thr
145                 150                 155
```

<210> SEQ ID NO 25
<211> LENGTH: 233
<212> TYPE: PRT
<213> ORGANISM: Artificial Sequence
<220> FEATURE:
<223> OTHER INFORMATION: PVA Protease C19Q/C110S/C181S/C211S mutant

<400> SEQUENCE: 25

```
Ser Thr Ser Met Phe Arg Gly Val Arg Asp Tyr Asn Pro Ile Ser Ser
1               5                   10                  15

Val Ile Gln Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

Val Arg Asn Asn Gly Ser Leu Thr Val Arg Ser Gln Met Gly Val Phe
    50                  55                  60

Lys Val Asn Ser Thr Val Thr Leu Gln Met Arg Pro Val Glu Gly Arg
65                  70                  75                  80

Asp Val Leu Ile Ile Lys Met Pro Lys Asp Phe Pro Pro Phe Pro Gln
                85                  90                  95

Arg Leu Lys Phe Arg Gln Pro Thr His Ser Glu Lys Val Ser Leu Ile
            100                 105                 110
```

```
Leu Thr Asn Phe Gln Gln Lys Ser Ser Ser Met Val Ser Glu Thr
        115                 120                 125

Ser His Ile Ile Pro Lys Glu Asn Thr Tyr Phe Trp Lys His Trp Ile
    130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Ser Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Ser Trp Gly Ser Phe His Leu Gln Asp Ser Lys Pro Thr Lys
    210                 215                 220

Glu Phe Lys Thr Val Lys Leu Val Thr
225                 230

<210> SEQ ID NO 26
<211> LENGTH: 233
<212> TYPE: PRT
<213> ORGANISM: Artificial Sequence
<220> FEATURE:
<223> OTHER INFORMATION: PVA Protease C19R/C110S/C181S/C211S mutant

<400> SEQUENCE: 26

Ser Thr Ser Met Phe Arg Gly Val Arg Asp Tyr Asn Pro Ile Ser Ser
1               5                   10                  15

Val Ile Arg Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

Val Arg Asn Asn Gly Ser Leu Thr Val Arg Ser Gln Met Gly Val Phe
    50                  55                  60

Lys Val Asn Ser Thr Val Thr Leu Gln Met Arg Pro Val Glu Gly Arg
65                  70                  75                  80

Asp Val Leu Ile Ile Lys Met Pro Lys Asp Phe Pro Phe Pro Pro Gln
                85                  90                  95

Arg Leu Lys Phe Arg Gln Pro Thr His Ser Glu Lys Val Ser Leu Ile
            100                 105                 110

Leu Thr Asn Phe Gln Gln Lys Ser Ser Ser Met Val Ser Glu Thr
        115                 120                 125

Ser His Ile Ile Pro Lys Glu Asn Thr Tyr Phe Trp Lys His Trp Ile
    130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Ser Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Ser Trp Gly Ser Phe His Leu Gln Asp Ser Lys Pro Thr Lys
    210                 215                 220

Glu Phe Lys Thr Val Lys Leu Val Thr
225                 230
```

<210> SEQ ID NO 27
<211> LENGTH: 233
<212> TYPE: PRT
<213> ORGANISM: Artificial Sequence
<220> FEATURE:
<223> OTHER INFORMATION: PVA Protease C19T/C110S/C181S/C211S mutant

<400> SEQUENCE: 27

```
Ser Thr Ser Met Phe Arg Gly Val Arg Asp Tyr Asn Pro Ile Ser Ser
  1               5                  10                  15

Val Ile Thr Gln Leu Glu Asn Glu Ser Glu Gly Arg Thr Thr Gln Leu
             20                  25                  30

Phe Gly Leu Gly Phe Gly Pro Phe Ile Ile Thr Asn Gln His Leu Phe
         35                  40                  45

Val Arg Asn Asn Gly Ser Leu Thr Val Arg Ser Gln Met Gly Val Phe
     50                  55                  60

Lys Val Asn Ser Thr Val Thr Leu Gln Met Arg Pro Val Glu Gly Arg
 65                  70                  75                  80

Asp Val Leu Ile Ile Lys Met Pro Lys Asp Phe Pro Pro Phe Pro Gln
                 85                  90                  95

Arg Leu Lys Phe Arg Gln Pro Thr His Ser Glu Lys Val Ser Leu Ile
            100                 105                 110

Leu Thr Asn Phe Gln Gln Lys Ser Ser Ser Met Val Ser Glu Thr
            115                 120                 125

Ser His Ile Ile Pro Lys Glu Asn Thr Tyr Phe Trp Lys His Trp Ile
        130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Ser Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Ser Trp Gly Ser Phe His Leu Gln Asp Ser Lys Pro Thr Lys
    210                 215                 220

Glu Phe Lys Thr Val Lys Leu Val Thr
225                 230
```

<210> SEQ ID NO 28
<211> LENGTH: 156
<212> TYPE: PRT
<213> ORGANISM: Artificial Sequence
<220> FEATURE:
<223> OTHER INFORMATION: PVA Protease C19V/C110S/C181S/C211S mutant

<400> SEQUENCE: 28

```
Glu Gly Arg Asp Val Leu Ile Ile Lys Met Pro Lys Asp Phe Pro Pro
  1               5                  10                  15

Phe Pro Gln Arg Leu Lys Phe Arg Gln Pro Thr His Ser Glu Lys Val
             20                  25                  30

Ser Leu Ile Leu Thr Asn Phe Gln Gln Lys Ser Ser Ser Met Val
         35                  40                  45

Ser Glu Thr Ser His Ile Ile Pro Lys Glu Asn Thr Tyr Phe Trp Lys
     50                  55                  60

His Trp Ile Ser Thr Lys Glu Gly His Cys Gly Ser Pro Ile Val Ser
```

```
65                  70                  75                  80
Thr Thr Asp Gly Ala Ile Leu Gly Ile His Ser Leu Ser Asn Met Thr
                85                  90                  95
Asn Thr Ser Asn Tyr Phe Ala Ser Phe Pro Lys Gly Phe Thr Glu Thr
                100                 105                 110
Tyr Leu Ala Thr Glu Ser Ala His Glu Trp Val Lys Gly Trp Lys Phe
                115                 120                 125
Asn Ala Ser Asn Val Ser Trp Gly Ser Phe His Leu Gln Asp Ser Lys
    130                 135                 140
Pro Thr Lys Glu Phe Lys Thr Val Lys Leu Val Thr
145                 150                 155

<210> SEQ ID NO 29
<211> LENGTH: 156
<212> TYPE: PRT
<213> ORGANISM: Artificial Sequence
<220> FEATURE:
<223> OTHER INFORMATION: PVA Protease C19W/C110S/C181S/C211S mutant

<400> SEQUENCE: 29

Glu Gly Arg Asp Val Leu Ile Ile Lys Met Pro Lys Asp Phe Pro Pro
1               5                   10                  15
Phe Pro Gln Arg Leu Lys Phe Arg Gln Pro Thr His Ser Glu Lys Val
                20                  25                  30
Ser Leu Ile Leu Thr Asn Phe Gln Gln Lys Ser Ser Ser Ser Met Val
                35                  40                  45
Ser Glu Thr Ser His Ile Ile Pro Lys Glu Asn Thr Tyr Phe Trp Lys
    50                  55                  60
His Trp Ile Ser Thr Lys Glu Gly His Cys Gly Ser Pro Ile Val Ser
65                  70                  75                  80
Thr Thr Asp Gly Ala Ile Leu Gly Ile His Ser Leu Ser Asn Met Thr
                85                  90                  95
Asn Thr Ser Asn Tyr Phe Ala Ser Phe Pro Lys Gly Phe Thr Glu Thr
                100                 105                 110
Tyr Leu Ala Thr Glu Ser Ala His Glu Trp Val Lys Gly Trp Lys Phe
                115                 120                 125
Asn Ala Ser Asn Val Ser Trp Gly Ser Phe His Leu Gln Asp Ser Lys
    130                 135                 140
Pro Thr Lys Glu Phe Lys Thr Val Lys Leu Val Thr
145                 150                 155

<210> SEQ ID NO 30
<211> LENGTH: 156
<212> TYPE: PRT
<213> ORGANISM: Artificial Sequence
<220> FEATURE:
<223> OTHER INFORMATION: PVA Protease C19Y/C110S/C181S/C211S mutant

<400> SEQUENCE: 30

Glu Gly Arg Asp Val Leu Ile Ile Lys Met Pro Lys Asp Phe Pro Pro
1               5                   10                  15
Phe Pro Gln Arg Leu Lys Phe Arg Gln Pro Thr His Ser Glu Lys Val
                20                  25                  30
Ser Leu Ile Leu Thr Asn Phe Gln Gln Lys Ser Ser Ser Ser Met Val
                35                  40                  45
Ser Glu Thr Ser His Ile Ile Pro Lys Glu Asn Thr Tyr Phe Trp Lys
    50                  55                  60
```

```
His Trp Ile Ser Thr Lys Glu Gly His Cys Gly Ser Pro Ile Val Ser
 65                  70                  75                  80

Thr Thr Asp Gly Ala Ile Leu Gly Ile His Ser Leu Ser Asn Met Thr
                 85                  90                  95

Asn Thr Ser Asn Tyr Phe Ala Ser Phe Pro Lys Gly Phe Thr Glu Thr
            100                 105                 110

Tyr Leu Ala Thr Glu Ser Ala His Glu Trp Val Lys Gly Trp Lys Phe
        115                 120                 125

Asn Ala Ser Asn Val Ser Trp Gly Ser Phe His Leu Gln Asp Ser Lys
    130                 135                 140

Pro Thr Lys Glu Phe Lys Thr Val Lys Leu Val Thr
145                 150                 155
```

<210> SEQ ID NO 31
<211> LENGTH: 233
<212> TYPE: PRT
<213> ORGANISM: Artificial Sequence
<220> FEATURE:
<223> OTHER INFORMATION: PVA Protease C110S/C151S/C181S/C211S Mutant

<400> SEQUENCE: 31

```
Ser Thr Ser Met Phe Arg Gly Val Arg Asp Tyr Asn Pro Ile Ser Ser
 1               5                  10                  15

Val Ile Cys Gln Leu Glu Asn Glu Ser Glu Gly Arg Thr Thr Gln Leu
                20                  25                  30

Phe Gly Leu Gly Phe Gly Pro Phe Ile Ile Thr Asn Gln His Leu Phe
            35                  40                  45

Val Arg Asn Asn Gly Ser Leu Thr Val Arg Ser Gln Met Gly Val Phe
        50                  55                  60

Lys Val Asn Ser Thr Val Thr Leu Gln Met Arg Pro Val Glu Gly Arg
 65                  70                  75                  80

Asp Val Leu Ile Ile Lys Met Pro Lys Asp Phe Pro Pro Phe Pro Gln
                 85                  90                  95

Arg Leu Lys Phe Arg Gln Pro Thr His Ser Glu Lys Val Ser Leu Ile
            100                 105                 110

Leu Thr Asn Phe Gln Gln Lys Ser Ser Ser Met Val Ser Glu Thr
        115                 120                 125

Ser His Ile Ile Pro Lys Glu Asn Thr Tyr Phe Trp Lys His Trp Ile
    130                 135                 140

Ser Thr Lys Glu Gly His Ser Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Ser Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Ser Trp Gly Ser Phe His Leu Gln Asp Ser Lys Pro Thr Lys
    210                 215                 220

Glu Phe Lys Thr Val Lys Leu Val Thr
225                 230
```

<210> SEQ ID NO 32
<211> LENGTH: 233
<212> TYPE: PRT
<213> ORGANISM: Artificial Sequence
<220> FEATURE:

<223> OTHER INFORMATION: PVA Protease C181S/C211S mutant

<400> SEQUENCE: 32

```
Ser Thr Ser Met Phe Arg Gly Val Arg Asp Tyr Asn Pro Ile Ser Ser
1               5                   10                  15

Val Ile Cys Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

Val Arg Asn Asn Gly Ser Leu Thr Val Arg Ser Gln Met Gly Val Phe
    50                  55                  60

Lys Val Asn Ser Thr Val Thr Leu Gln Met Arg Pro Val Glu Gly Arg
65                  70                  75                  80

Asp Val Leu Ile Ile Lys Met Pro Lys Asp Phe Pro Pro Phe Pro Gln
                85                  90                  95

Arg Leu Lys Phe Arg Gln Pro Thr His Ser Glu Lys Val Cys Leu Ile
            100                 105                 110

Leu Thr Asn Phe Gln Gln Lys Ser Ser Ser Met Val Ser Glu Thr
        115                 120                 125

Ser His Ile Ile Pro Lys Glu Asn Thr Tyr Phe Trp Lys His Trp Ile
    130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Ser Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Ser Trp Gly Ser Phe His Leu Gln Asp Ser Lys Pro Thr Lys
    210                 215                 220

Glu Phe Lys Thr Val Lys Leu Val Thr
225                 230
```

<210> SEQ ID NO 33
<211> LENGTH: 156
<212> TYPE: PRT
<213> ORGANISM: Artificial Sequence
<220> FEATURE:
<223> OTHER INFORMATION: PVA Protease C19V/C110S/C151S/C181S/C211S
      mutant

<400> SEQUENCE: 33

```
Glu Gly Arg Asp Val Leu Ile Ile Lys Met Pro Lys Asp Phe Pro Pro
1               5                   10                  15

Phe Pro Gln Arg Leu Lys Phe Arg Gln Pro Thr His Ser Glu Lys Val
            20                  25                  30

Ser Leu Ile Leu Thr Asn Phe Gln Gln Lys Ser Ser Ser Met Val
        35                  40                  45

Ser Glu Thr Ser His Ile Ile Pro Lys Glu Asn Thr Tyr Phe Trp Lys
    50                  55                  60

His Trp Ile Ser Thr Lys Glu Gly His Ser Gly Ser Pro Ile Val Ser
65                  70                  75                  80

Thr Thr Asp Gly Ala Ile Leu Gly Ile His Ser Leu Ser Asn Met Thr
                85                  90                  95

Asn Thr Ser Asn Tyr Phe Ala Ser Phe Pro Lys Gly Phe Thr Glu Thr
```

```
                    100                 105                 110
Tyr Leu Ala Thr Glu Ser Ala His Glu Trp Val Lys Gly Trp Lys Phe
            115                 120                 125

Asn Ala Ser Asn Val Ser Trp Gly Ser Phe His Leu Gln Asp Ser Lys
        130                 135                 140

Pro Thr Lys Glu Phe Lys Thr Val Lys Leu Val Thr
145                 150                 155

<210> SEQ ID NO 34
<211> LENGTH: 233
<212> TYPE: PRT
<213> ORGANISM: Artificial Sequence
<220> FEATURE:
<223> OTHER INFORMATION: PVA Protease C151A mutant

<400> SEQUENCE: 34

Ser Thr Ser Met Phe Arg Gly Val Arg Asp Tyr Asn Pro Ile Ser Ser
1               5                   10                  15

Val Ile Cys Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

Val Arg Asn Asn Gly Ser Leu Thr Val Arg Ser Gln Met Gly Val Phe
    50                  55                  60

Lys Val Asn Ser Thr Val Thr Leu Gln Met Arg Pro Val Glu Gly Arg
65                  70                  75                  80

Asp Val Leu Ile Ile Lys Met Pro Lys Asp Phe Pro Pro Phe Pro Gln
                85                  90                  95

Arg Leu Lys Phe Arg Gln Pro Thr His Ser Glu Lys Val Cys Leu Ile
            100                 105                 110

Leu Thr Asn Phe Gln Gln Lys Ser Ser Ser Met Val Ser Glu Thr
        115                 120                 125

Ser His Ile Ile Pro Lys Glu Asn Thr Tyr Phe Trp Lys His Trp Ile
    130                 135                 140

Ser Thr Lys Glu Gly His Ala Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Cys Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Cys Trp Gly Ser Phe His Leu Gln Asp Ser Lys Pro Thr Lys
    210                 215                 220

Glu Phe Lys Thr Val Lys Leu Val Thr
225                 230

<210> SEQ ID NO 35
<211> LENGTH: 241
<212> TYPE: PRT
<213> ORGANISM: Artificial Sequence
<220> FEATURE:
<223> OTHER INFORMATION: PVA Protease with N-terminal 6x-His tag

<400> SEQUENCE: 35

Met Gly His His His His His His Ser Thr Ser Met Phe Arg Gly Val
1               5                   10                  15
```

```
Arg Asp Tyr Asn Pro Ile Ser Val Ile Cys Gln Leu Glu Asn Glu
             20                  25                  30

Ser Glu Gly Arg Thr Thr Gln Leu Phe Gly Leu Gly Phe Gly Pro Phe
         35                  40                  45

Ile Ile Thr Asn Gln His Leu Phe Val Arg Asn Asn Gly Ser Leu Thr
 50                  55                  60

Val Arg Ser Gln Met Gly Val Phe Lys Val Asn Ser Thr Val Thr Leu
 65                  70                  75                  80

Gln Met Arg Pro Val Glu Gly Arg Asp Val Leu Ile Ile Lys Met Pro
                 85                  90                  95

Lys Asp Phe Pro Pro Phe Pro Gln Arg Leu Lys Phe Arg Gln Pro Thr
                100                 105                 110

His Ser Glu Lys Val Cys Leu Ile Leu Thr Asn Phe Gln Gln Lys Ser
            115                 120                 125

Ser Ser Ser Met Val Ser Glu Thr Ser His Ile Ile Pro Lys Glu Asn
        130                 135                 140

Thr Tyr Phe Trp Lys His Trp Ile Ser Thr Lys Glu Gly His Cys Gly
145                 150                 155                 160

Ser Pro Ile Val Ser Thr Thr Asp Gly Ala Ile Leu Gly Ile His Ser
                165                 170                 175

Leu Ser Asn Met Thr Asn Thr Ser Asn Tyr Phe Ala Cys Phe Pro Lys
            180                 185                 190

Gly Phe Thr Glu Thr Tyr Leu Ala Thr Glu Ser Ala His Glu Trp Val
        195                 200                 205

Lys Gly Trp Lys Phe Asn Ala Ser Asn Val Cys Trp Gly Ser Phe His
210                 215                 220

Leu Gln Asp Ser Lys Pro Thr Lys Glu Phe Lys Thr Val Lys Leu Val
225                 230                 235                 240

Thr

<210> SEQ ID NO 36
<211> LENGTH: 239
<212> TYPE: PRT
<213> ORGANISM: Artificial Sequence
<220> FEATURE:
<223> OTHER INFORMATION: PVA Protease with C-terminal 6x-His tag

<400> SEQUENCE: 36

Ser Thr Ser Met Phe Arg Gly Val Arg Asp Tyr Asn Pro Ile Ser Ser
 1               5                  10                  15

Val Ile Cys Gln Leu Glu Asn Glu Ser Glu Gly Arg Thr Thr Gln Leu
             20                  25                  30

Phe Gly Leu Gly Phe Gly Pro Phe Ile Ile Thr Asn Gln His Leu Phe
         35                  40                  45

Val Arg Asn Asn Gly Ser Leu Thr Val Arg Ser Gln Met Gly Val Phe
 50                  55                  60

Lys Val Asn Ser Thr Val Thr Leu Gln Met Arg Pro Val Glu Gly Arg
 65                  70                  75                  80

Asp Val Leu Ile Ile Lys Met Pro Lys Asp Phe Pro Pro Phe Pro Gln
                 85                  90                  95

Arg Leu Lys Phe Arg Gln Pro Thr His Ser Glu Lys Val Cys Leu Ile
                100                 105                 110

Leu Thr Asn Phe Gln Gln Lys Ser Ser Ser Ser Met Val Ser Glu Thr
            115                 120                 125

Ser His Ile Ile Pro Lys Glu Asn Thr Tyr Phe Trp Lys His Trp Ile
```

```
                130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Cys Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Cys Trp Gly Ser Phe His Leu Gln Asp Ser Lys Pro Thr Lys
    210                 215                 220

Glu Phe Lys Thr Val Lys Leu Val Thr His His His His His His
225                 230                 235

<210> SEQ ID NO 37
<211> LENGTH: 239
<212> TYPE: PRT
<213> ORGANISM: Artificial Sequence
<220> FEATURE:
<223> OTHER INFORMATION: PVA C151S Protease with C-terminal 6x-His tag

<400> SEQUENCE: 37

Ser Thr Ser Met Phe Arg Gly Val Arg Asp Tyr Asn Pro Ile Ser Ser
1               5                   10                  15

Val Ile Cys Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

Val Arg Asn Asn Gly Ser Leu Thr Val Arg Ser Gln Met Gly Val Phe
    50                  55                  60

Lys Val Asn Ser Thr Val Thr Leu Gln Met Arg Pro Val Glu Gly Arg
65                  70                  75                  80

Asp Val Leu Ile Ile Lys Met Pro Lys Asp Phe Pro Pro Phe Pro Gln
                85                  90                  95

Arg Leu Lys Phe Arg Gln Pro Thr His Ser Glu Lys Val Cys Leu Ile
            100                 105                 110

Leu Thr Asn Phe Gln Gln Lys Ser Ser Ser Met Val Ser Glu Thr
        115                 120                 125

Ser His Ile Ile Pro Lys Glu Asn Thr Tyr Phe Trp Lys His Trp Ile
    130                 135                 140

Ser Thr Lys Glu Gly His Ser Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Cys Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Cys Trp Gly Ser Phe His Leu Gln Asp Ser Lys Pro Thr Lys
    210                 215                 220

Glu Phe Lys Thr Val Lys Leu Val Thr His His His His His His
225                 230                 235

<210> SEQ ID NO 38
<211> LENGTH: 239
<212> TYPE: PRT
```

<213> ORGANISM: Artificial Sequence
<220> FEATURE:
<223> OTHER INFORMATION: PVA Protease C19V/C110S/C181S/C211S with
      C-terminal 6x-His tag

<400> SEQUENCE: 38

```
Ser Thr Ser Met Phe Arg Gly Val Arg Asp Tyr Asn Pro Ile Ser Ser
1               5                   10                  15

Val Ile Val Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

Val Arg Asn Asn Gly Ser Leu Thr Val Arg Ser Gln Met Gly Val Phe
    50                  55                  60

Lys Val Asn Ser Thr Val Thr Leu Gln Met Arg Pro Val Glu Gly Arg
65                  70                  75                  80

Asp Val Leu Ile Ile Lys Met Pro Lys Asp Phe Pro Pro Phe Pro Gln
                85                  90                  95

Arg Leu Lys Phe Arg Gln Pro Thr His Ser Glu Lys Val Ser Leu Ile
            100                 105                 110

Leu Thr Asn Phe Gln Gln Lys Ser Ser Ser Met Val Ser Glu Thr
        115                 120                 125

Ser His Ile Ile Pro Lys Glu Asn Thr Tyr Phe Trp Lys His Trp Ile
    130                 135                 140

Ser Thr Lys Glu Gly His Cys Gly Ser Pro Ile Val Ser Thr Thr Asp
145                 150                 155                 160

Gly Ala Ile Leu Gly Ile His Ser Leu Ser Asn Met Thr Asn Thr Ser
                165                 170                 175

Asn Tyr Phe Ala Ser Phe Pro Lys Gly Phe Thr Glu Thr Tyr Leu Ala
            180                 185                 190

Thr Glu Ser Ala His Glu Trp Val Lys Gly Trp Lys Phe Asn Ala Ser
        195                 200                 205

Asn Val Ser Trp Gly Ser Phe His Leu Gln Asp Ser Lys Pro Thr Lys
    210                 215                 220

Glu Phe Lys Thr Val Lys Leu Val Thr His His His His His His
225                 230                 235
```

<210> SEQ ID NO 39
<211> LENGTH: 239
<212> TYPE: PRT
<213> ORGANISM: Artificial Sequence
<220> FEATURE:
<223> OTHER INFORMATION: PVA Protease C19V/C110S/C151S/C181S/C211S with
      C-terminal 6x-His tag

<400> SEQUENCE: 39

```
Ser Thr Ser Met Phe Arg Gly Val Arg Asp Tyr Asn Pro Ile Ser Ser
1               5                   10                  15

Val Ile Val Gln Leu Glu Asn Glu Ser Glu Gly Arg Thr Thr Gln Leu
            20                  25                  30

Phe Gly Leu Gly Phe Gly Pro Phe Ile Ile Thr Asn Gln His Leu Phe
        35                  40                  45

Val Arg Asn Asn Gly Ser Leu Thr Val Arg Ser Gln Met Gly Val Phe
    50                  55                  60

Lys Val Asn Ser Thr Val Thr Leu Gln Met Arg Pro Val Glu Gly Arg
65                  70                  75                  80

Asp Val Leu Ile Ile Lys Met Pro Lys Asp Phe Pro Pro Phe Pro Gln
```

```
                    85                  90                  95
Arg Leu Lys Phe Arg Gln Pro Thr His Ser Glu Lys Val Ser Leu Ile
            100                 105                 110

Leu Thr Asn Phe Gln Gln Lys Ser Ser Ser Met Val Ser Glu Thr
        115                 120                 125

Ser His Ile Ile Pro Lys Glu Asn Thr Tyr Phe Trp Lys His Trp Ile
145             150                 155                 160

Ser Thr Lys Glu Gly His Ser Gly Ser Pro Ile Val Ser Thr Thr Asp
145             150                 155                 160

Gly Ala Ile Leu Gly Ile His Ser Leu Ser Asn Met Thr Asn Thr Ser
                165                 170                 175

Asn Tyr Phe Ala Ser Phe Pro Lys Gly Phe Thr Glu Thr Tyr Leu Ala
                180                 185                 190

Thr Glu Ser Ala His Glu Trp Val Lys Gly Trp Lys Phe Asn Ala Ser
            195                 200                 205

Asn Val Ser Trp Gly Ser Phe His Leu Gln Asp Ser Lys Pro Thr Lys
        210                 215                 220

Glu Phe Lys Thr Val Lys Leu Val Thr His His His His His His
225                 230                 235
```

<210> SEQ ID NO 40
<211> LENGTH: 699
<212> TYPE: DNA
<213> ORGANISM: Potato Virus
<220> FEATURE:
<223> OTHER INFORMATION: NIa protease

<400> SEQUENCE: 40

```
tctacctcta tgttccgtgg tgttcgtgac tacaacccga tctcttctgt tatctgccag     60
ctggaaaacg aatctgaagg tcgtaccacc cagctgttcg gtctgggttt cggtccgttc    120
atcatcacca ccagcacct gttcgttcgt aacaacggtt ctctgaccgt tcgttctcag    180
atgggtgttt tcaaagttaa ctctaccgtt accctgcaga tgcgtccggt tgaaggtcgt    240
gacgttctga tcatcaaaat gccgaaagac ttcccgccgt tcccgcagcg tctgaaattc    300
cgtcagccga cccactctga aaagtttgc ctgatcctga ccaacttcca gcagaaatct    360
tcttcttcta tggttctga acctctcac atcatcccga agaaaacac ctacttctgg    420
aaacactgga tctctaccaa agaaggtcac tcgggttctc cgatcgtttc taccaccgac    480
ggtgcgatcc tgggtatcca ctctctgtct aacatgacca cacctctaa ctacttcgcg    540
tgcttcccga aggtttcac cgaaacctac ctggcgaccg aatctgcgca cgaatgggtt    600
aaaggttgga aattcaacgc gtctaacgtt tgctggggtt ctttccacct gcaggactct    660
aaaccgacca agaattcaa aaccgttaaa ctggttacc                           699
```

<210> SEQ ID NO 41
<211> LENGTH: 699
<212> TYPE: DNA
<213> ORGANISM: Artificial Sequence
<220> FEATURE:
<223> OTHER INFORMATION: PVA C151S mutant

<400> SEQUENCE: 41

```
tctacctcta tgttccgtgg tgttcgtgac tacaacccga tctcttctgt tatctgccag     60
ctggaaaacg aatctgaagg tcgtaccacc cagctgttcg gtctgggttt cggtccgttc    120
atcatcacca ccagcacct gttcgttcgt aacaacggtt ctctgaccgt tcgttctcag    180
```

```
atgggtgttt tcaaagttaa ctctaccgtt accctgcaga tgcgtccggt tgaaggtcgt      240
gacgttctga tcatcaaaat gccgaaagac ttcccgccgt tcccgcagcg tctgaaattc      300
cgtcagccga cccactctga aaaagtttgc ctgatcctga ccaacttcca gcagaaatct      360
tcttcttcta tggtttctga aacctctcac atcatcccga agaaaacac ctacttctgg       420 aaacactgga tctctaccaa agaaggtcac agcggttctc cgatcgtttc taccaccgac      480
ggtgcgatcc tgggtatcca ctctctgtct aacatgacca cacctctaa ctacttcgcg       540 tgcttcccga aggtttcac cgaaacctac ctggcgaccg aatctgcgca cgaatgggtt       600
aaaggttgga aattcaacgc gtctaacgtt tgctggggtt ctttccacct gcaggactct      660
aaaccgacca agaattcaa aaccgttaaa ctggttacc                               699
```

<210> SEQ ID NO 42
<211> LENGTH: 699
<212> TYPE: DNA
<213> ORGANISM: Artificial Sequence
<220> FEATURE:
<223> OTHER INFORMATION: PVA Protease C19V/C110S/C181S/C211S mutant

<400> SEQUENCE: 42

```
tctacctcta tgttccgtgg tgttcgtgac tacaacccga tctcttctgt tatcgttcag      60
ctggaaaacg aatctgaagg tcgtaccacc cagctgttcg gtctgggttt cggtccgttc      120
atcatcacca ccagcacct gttcgttcgt aacaacggtt ctctgaccgt tcgttctcag       180
atgggtgttt tcaaagttaa ctctaccgtt accctgcaga tgcgtccggt tgaaggtcgt      240
gacgttctga tcatcaaaat gccgaaagac ttcccgccgt tcccgcagcg tctgaaattc      300
cgtcagccga cccactctga aaaagttagc ctgatcctga ccaacttcca gcagaaatct      360
tcttcttcta tggtttctga aacctctcac atcatcccga agaaaacac ctacttctgg       420 aaacactgga tctctaccaa agaaggtcac tgcggttctc cgatcgtttc taccaccgac      480
ggtgcgatcc tgggtatcca ctctctgtct aacatgacca cacctctaa ctacttcgcg       540 agcttcccga aggtttcac cgaaacctac ctggcgaccg aatctgcgca cgaatgggtt       600
aaaggttgga aattcaacgc gtctaacgtt agctggggtt ctttccacct gcaggactct      660
aaaccgacca agaattcaa aaccgttaaa ctggttacc                               699
```

<210> SEQ ID NO 43
<211> LENGTH: 699
<212> TYPE: DNA
<213> ORGANISM: Artificial Sequence
<220> FEATURE:
<223> OTHER INFORMATION: PVA Protease C19V/C110S/C151S/C181S/C211S
      mutant

<400> SEQUENCE: 43

```
tctacctcta tgttccgtgg tgttcgtgac tacaacccga tctcttctgt tatcgttcag      60
ctggaaaacg aatctgaagg tcgtaccacc cagctgttcg gtctgggttt cggtccgttc      120
atcatcacca ccagcacct gttcgttcgt aacaacggtt ctctgaccgt tcgttctcag       180
atgggtgttt tcaaagttaa ctctaccgtt accctgcaga tgcgtccggt tgaaggtcgt      240
gacgttctga tcatcaaaat gccgaaagac ttcccgccgt tcccgcagcg tctgaaattc      300
cgtcagccga cccactctga aaaagttagc ctgatcctga ccaacttcca gcagaaatct      360
tcttcttcta tggtttctga aacctctcac atcatcccga agaaaacac ctacttctgg       420 aaacactgga tctctaccaa agaaggtcac agcggttctc cgatcgtttc taccaccgac      480
```

```
ggtgcgatcc tgggtatcca ctctctgtct aacatgacca acacctctaa ctacttcgcg    540
agcttcccga aggtttcac cgaaacctac ctggcgaccg aatctgcgca cgaatgggtt    600
aaaggttgga aattcaacgc gtctaacgtt agctggggtt ctttccacct gcaggactct   660
aaaccgacca agaattcaa aaccgttaaa ctggttacc                            699
```

```
<210> SEQ ID NO 44
<211> LENGTH: 723
<212> TYPE: DNA
<213> ORGANISM: Artificial Sequence
<220> FEATURE:
<223> OTHER INFORMATION: PVA Protease with N-terminal 6x-His tag

<400> SEQUENCE: 44
atgggccacc atcaccatca ccattctacc tctatgttcc gtggtgttcg tgactacaac     60
ccgatctctt ctgttatctg ccagctggaa acgaatctg aaggtcgtac cacccagctg    120
ttcggtctgg gtttcggtcc gttcatcatc accaaccagc acctgttcgt tcgtaacaac   180
ggttctctga ccgttcgttc tcagatgggt gttttcaaag ttaactctac cgttaccctg   240
cagatgcgtc cggttgaagg tcgtgacgtt ctgatcatca aaatgccgaa agacttcccg   300 ccgttccgc agcgtctgaa attccgtcag ccgacccact ctgaaaaagt tgcctgatc    360 ctgaccaact ccagcagaa atcttcttct tctatggttt ctgaaacctc tcacatcatc   420
ccgaaagaaa acacctactt ctggaaacac tggatctcta ccaaagaagg tcactgcggt   480
tctccgatcg tttctaccac cgacggtgcg atcctgggta ccactctct gtctaacatg    540 accaacaccct ctaactactt cgcgtgcttc ccgaaaggtt tcaccgaaac ctacctggcg   600
accgaatctg cgcacgaatg ggttaaaggt tggaaattca acgcgtctaa cgtttgctgg    660
ggttctttcc acctgcagga ctctaaaccg accaagaat caaaaccgt taaactggtt    720 acc                                                                 723
```

```
<210> SEQ ID NO 45
<211> LENGTH: 717
<212> TYPE: DNA
<213> ORGANISM: Artificial Sequence
<220> FEATURE:
<223> OTHER INFORMATION: PVA Protease with C-terminal 6x-His tag

<400> SEQUENCE: 45
tctacctcta tgttccgtgg tgttcgtgac tacaacccga tctcttctgt tatctgccag    60
ctggaaaacg aatctgaagg tcgtaccacc cagctgttcg gtctgggttt cggtccgttc   120
atcatcacca accagcacct gttcgttcgt aacaacggtt ctctgaccgt tcgttctcag   180
atgggtgttt tcaaagttaa ctctaccgtt accctgcaga tgcgtccggt tgaaggtcgt    240
gacgttctga tcatcaaaat gccgaaagac ttcccgccgt tccgcagcg tctgaaattc    300 cgtcagccga cccactctga aaagtttgc ctgatcctga ccaacttcca gcagaaatct   360
tcttcttcta tggtttctga aacctctcac atcatcccga agaaaacac ctacttctgg    420 aaacactgga tctctaccaa agaaggtcac tgcggttctc cgatcgtttc taccaccgac   480
ggtgcgatcc tgggtatcca ctctctgtct aacatgacca acacctctaa ctacttcgcg   540
tgcttcccga aggtttcac cgaaacctac ctggcgaccg aatctgcgca cgaatgggtt   600
aaaggttgga aattcaacgc gtctaacgtt tgctggggtt ctttccacct gcaggactct   660
aaaccgacca agaattcaa aaccgttaaa ctggttaccc accatcacca tcaccat      717
```

<210> SEQ ID NO 46
<211> LENGTH: 717
<212> TYPE: DNA
<213> ORGANISM: Artificial Sequence
<220> FEATURE:
<223> OTHER INFORMATION: PVA C151S mutant with C-terminal 6x-His tag

<400> SEQUENCE: 46

```
tctacctcta tgttccgtgg tgttcgtgac tacaacccga tctcttctgt tatctgccag      60
ctggaaaacg aatctgaagg tcgtaccacc cagctgttcg gtctgggttt cggtccgttc     120
atcatcacca accagcacct gttcgttcgt aacaacggtt ctctgaccgt tcgttctcag     180
atgggtgttt tcaaagttaa ctctaccgtt accctgcaga tgcgtccggt tgaaggtcgt     240
gacgttctga tcatcaaaat gccgaaagac ttcccgccgt tcccgcagcg tctgaaattc     300
cgtcagccga cccactctga aaagtttgc ctgatcctga ccaacttcca gcagaaatct     360
tcttcttcta tggtttctga aacctctcac atcatcccga agaaaacac ctacttctgg      420
aaacactgga tctctaccaa agaaggtcac agcggttctc cgatcgtttc taccaccgac     480
ggtgcgatcc tgggtatcca ctctctgtct aacatgacca cacctctaa ctacttcgcg      540
tgcttcccga aggttttcac cgaaacctac ctggcgaccg aatctgcgca cgaatgggtt     600
aaaggttgga attcaacgc gtctaacgtt tgctggggtt ctttccacct gcaggactct     660
aaaccgacca agaattcaa aaccgttaaa ctggttaccc accatcacca tcaccat       717
```

<210> SEQ ID NO 47
<211> LENGTH: 723
<212> TYPE: DNA
<213> ORGANISM: Artificial Sequence
<220> FEATURE:
<223> OTHER INFORMATION: PVA Protease C19V/C110S/C181S/C211S mutant with
      C-terminal 6x-His tag

<400> SEQUENCE: 47

```
atgggctcta cctctatgtt ccgtggtgtt cgtgactaca acccgatctc ttctgttatc      60
gttcagctgg aaaacgaatc tgaaggtcgt accacccagc tgttcggtct gggtttcggt     120
ccgttcatca tcaccaacca gcacctgttc gttcgtaaca acggtctct gaccgttcgt      180
tctcagatgg gtgttttcaa agttaactct accgttaccc tgcagatgcg tccggttgaa     240
ggtcgtgacg ttctgatcat caaaatgccg aaagacttcc cgccgttccc gcagcgtctg     300
aaattccgtc agccgaccca ctctgaaaaa gttagcctga tcctgaccaa cttccagcag     360
aaatcttctt cttctatggt ttctgaaacc tctcacatca tcccgaaaga aaacacctac     420
ttctggaaac actggatctc taccaaagaa ggtcactgcg gttctccgat cgtttctacc     480
accgacggtg cgatcctggg tatccactct ctgtctaaca tgaccaacac ctctaactac     540
ttcgcgagct cccgaaagg tttcaccgaa acctacctgg cgaccgaatc tgcgcacgaa     600
tgggttaaag gttggaaatt caacgcgtct aacgttagct ggggttcttt ccacctgcag     660
gactctaaac cgaccaaaga attcaaaacc gttaaactgg ttacccacca tcaccatcac     720
cat                                                                  723
```

<210> SEQ ID NO 48
<211> LENGTH: 717
<212> TYPE: DNA
<213> ORGANISM: Artificial Sequence
<220> FEATURE:
<223> OTHER INFORMATION: PVA Protease C19V/C110S/C151S/C181S/C211S
      mutant with C-terminal 6x-His tag

<400> SEQUENCE: 48

```
tctacctcta tgttccgtgg tgttcgtgac tacaacccga tctcttctgt tatcgttcag      60
ctggaaaacg aatctgaagg tcgtaccacc cagctgttcg gtctgggttt cggtccgttc     120
atcatcacca accagcacct gttcgttcgt aacaacggtt ctctgaccgt tcgttctcag     180
atgggtgttt tcaaagttaa ctctaccgtt accctgcaga tgcgtccggt tgaaggtcgt     240
gacgttctga tcatcaaaat gccgaaagac ttcccgccgt tcccgcagcg tctgaaattc     300
cgtcagccga cccactctga aaaagttagc ctgatcctga ccaacttcca gcagaaatct     360
tcttcttcta tggtttctga aacctctcac atcatcccga agaaaacac  ctacttctgg     420
aaacactgga tctctaccaa agaaggtcac agcggttctc cgatcgtttc taccaccgac     480
ggtgcgatcc tgggtatcca ctctctgtct aacatgacca cacctctaa  ctacttcgcg     540
agcttcccga aaggtttcac cgaaacctac ctggcgaccg aatctgcgca cgaatgggtt     600
aaaggttgga aattcaacgc gtctaacgtt agctggggtt ctttccacct gcaggactct     660
aaaccgacca aagaattcaa aaccgttaaa ctggttaccc accatcacca tcaccat      717
```

<210> SEQ ID NO 49
<211> LENGTH: 47
<212> TYPE: DNA
<213> ORGANISM: Artificial Sequence
<220> FEATURE:
<223> OTHER INFORMATION: mutagenesis primer

<400> SEQUENCE: 49

```
ctaaccatgg gctctacctc tatgttccgt ggtgttcgtg actacaa                    47
```

<210> SEQ ID NO 50
<211> LENGTH: 51
<212> TYPE: DNA
<213> ORGANISM: Artificial Sequence
<220> FEATURE:
<223> OTHER INFORMATION: mutagenesis primer

<400> SEQUENCE: 50

```
gttactcgag ttattaatgg tgatggtgat ggtgggtaac cagtttaacg g               51
```

<210> SEQ ID NO 51
<211> LENGTH: 37
<212> TYPE: DNA
<213> ORGANISM: Artificial Sequence
<220> FEATURE:
<223> OTHER INFORMATION: mutagenesis primer

<400> SEQUENCE: 51

```
ctaccaaaga cggtcagagc ggttctccga tcgtttc                               37
```

<210> SEQ ID NO 52
<211> LENGTH: 37
<212> TYPE: DNA
<213> ORGANISM: Artificial Sequence
<220> FEATURE:
<223> OTHER INFORMATION: mutagenesis primer

<400> SEQUENCE: 52

```
gaaacgatcg gagaaccgct ctgaccgtct ttggtag                               37
```

<210> SEQ ID NO 53
<211> LENGTH: 39
<212> TYPE: DNA
<213> ORGANISM: Artificial Sequence
<220> FEATURE:
<223> OTHER INFORMATION: mutagenesis primer

<400> SEQUENCE: 53
ctctaccaaa gaaggtcacg ccggttctcc gatcgtttc                    39

<210> SEQ ID NO 54
<211> LENGTH: 39
<212> TYPE: DNA
<213> ORGANISM: Artificial Sequence
<220> FEATURE:
<223> OTHER INFORMATION: mutagenesis primer

<400> SEQUENCE: 54
gaaacgatcg gagaaccggc gtgaccttct ttggtagag                    39

<210> SEQ ID NO 55
<211> LENGTH: 45
<212> TYPE: DNA
<213> ORGANISM: Artificial Sequence
<220> FEATURE:
<223> OTHER INFORMATION: mutagenesis primer

<400> SEQUENCE: 55
cccgatctct tctgttatca gccagctgga aaacgaatct gaagg             45

<210> SEQ ID NO 56
<211> LENGTH: 45
<212> TYPE: DNA
<213> ORGANISM: Artificial Sequence
<220> FEATURE:
<223> OTHER INFORMATION: mutagenesis primer

<400> SEQUENCE: 56
ccttcagatt cgttttccag ctggctgata acagaagaga tcggg             45

<210> SEQ ID NO 57
<211> LENGTH: 44
<212> TYPE: DNA
<213> ORGANISM: Artificial Sequence
<220> FEATURE:
<223> OTHER INFORMATION: mutagenesis primer

<400> SEQUENCE: 57
cgacccactc tgaaaagtt agcctgatcc tgaccaactt ccag               44

<210> SEQ ID NO 58
<211> LENGTH: 44
<212> TYPE: DNA
<213> ORGANISM: Artificial Sequence
<220> FEATURE:
<223> OTHER INFORMATION: mutagenesis primer

<400> SEQUENCE: 58
ctggaagttg gtcaggatca ggctaacttt ttcagagtgg gtcg              44

<210> SEQ ID NO 59
<211> LENGTH: 41
<212> TYPE: DNA
<213> ORGANISM: Artificial Sequence
<220> FEATURE:
<223> OTHER INFORMATION: mutagenesis primer

<400> SEQUENCE: 59
cacctctaac tacttcgcga gcttcccgaa aggtttcacc g                 41

```
<210> SEQ ID NO 60
<211> LENGTH: 41
<212> TYPE: DNA
<213> ORGANISM: Artificial Sequence
<220> FEATURE:
<223> OTHER INFORMATION: mutagenesis primer

<400> SEQUENCE: 60
cggtgaaacc tttcgggaag ctcgcgaagt agttagaggt g                    41

<210> SEQ ID NO 61
<211> LENGTH: 37
<212> TYPE: DNA
<213> ORGANISM: Artificial Sequence
<220> FEATURE:
<223> OTHER INFORMATION: mutagenesis primer

<400> SEQUENCE: 61
caacgcgtct aacgttagct ggggttcttt ccacctg                         37

<210> SEQ ID NO 62
<211> LENGTH: 37
<212> TYPE: DNA
<213> ORGANISM: Artificial Sequence
<220> FEATURE:
<223> OTHER INFORMATION: mutagenesis primer

<400> SEQUENCE: 62
caggtggaaa gaaccccagc taacgttaga cgcgttg                         37

<210> SEQ ID NO 63
<211> LENGTH: 45
<212> TYPE: DNA
<213> ORGANISM: Artificial Sequence
<220> FEATURE:
<223> OTHER INFORMATION: mutagenesis primer
<220> FEATURE:
<221> NAME/KEY: unsure
<222> LOCATION: (21)...(21)
<223> OTHER INFORMATION: Wherein n at position (21) can be  a, c, t, or
      g
<220> FEATURE:
<221> NAME/KEY: unsure
<222> LOCATION: (22)...(22)
<223> OTHER INFORMATION: Wherein n at position (22) can be a, c, t, or g
<220> FEATURE:
<221> NAME/KEY: unsure
<222> LOCATION: (23)...(23)
<223> OTHER INFORMATION: Wherein k at position (23) can be  g or t

<400> SEQUENCE: 63
acccgatctc ttctgttatc nnkcagctgg aaaacgaatc tgaag                45

<210> SEQ ID NO 64
<211> LENGTH: 45
<212> TYPE: DNA
<213> ORGANISM: Artificial Sequence
<220> FEATURE:
<223> OTHER INFORMATION: mutagenesis primer
<220> FEATURE:
<221> NAME/KEY: unsure
<222> LOCATION: (23)...(23)
<223> OTHER INFORMATION: Wherein m at position (23) can be a or c
<220> FEATURE:
<221> NAME/KEY: unsure
<222> LOCATION: (24)...(24)
<223> OTHER INFORMATION: Wherein n at position (24) can be  a, c, t, or
      g
<220> FEATURE:
<221> NAME/KEY: unsure
```

```
<222> LOCATION: (25)...(25)
<223> OTHER INFORMATION: Wherein n at position (25) can be  a, c, t, or
      g

<400> SEQUENCE: 64
cttcagattc gttttccagc tgmnngataa cagaagagat cgggt                45

<210> SEQ ID NO 65
<211> LENGTH: 7
<212> TYPE: PRT
<213> ORGANISM: Artificial Sequence
<220> FEATURE:
<223> OTHER INFORMATION: Consensus NIa cleavage site, has
      N-glycosylation site

<400> SEQUENCE: 65

Glu Asn Val Thr Phe Gln Gly
 1               5

<210> SEQ ID NO 66
<211> LENGTH: 7
<212> TYPE: PRT
<213> ORGANISM: Artificial Sequence
<220> FEATURE:
<223> OTHER INFORMATION: Consensus NIa cleavage site without
      N-glycosylation site

<400> SEQUENCE: 66

Glu Asn Val Thr Phe Gln Gly
 1               5

<210> SEQ ID NO 67
<211> LENGTH: 145
<212> TYPE: PRT
<213> ORGANISM: Artificial Sequence
<220> FEATURE:
<223> OTHER INFORMATION: NIa protease fusion substrate with ENVTFQG
      recognition site

<400> SEQUENCE: 67

Met Gly Ser Ser His His His His His His Ser Ser Gly Leu Val Pro
 1               5                  10                  15

Arg Gly Ser His Met Thr Thr Glu Asn Val Thr Phe Gln Gly Ser Thr
            20                  25                  30

Ala Ile Gly Met Lys Glu Thr Ala Ala Lys Phe Glu Arg Gln His
        35                  40                  45

Met Asp Ser Pro Asp Leu Gly Thr Leu Pro Ala Pro Lys Asn Leu Val
    50                  55                  60

Val Ser Glu Val Thr Glu Asp Ser Leu Arg Leu Ser Trp Thr Ala Pro
65                  70                  75                  80

Asp Ala Ala Phe Asp Ser Phe Leu Ile Gln Tyr Gln Glu Ser Glu Lys
                85                  90                  95

Val Gly Glu Ala Ile Asn Leu Thr Val Pro Gly Ser Glu Arg Ser Tyr
            100                 105                 110

Asp Leu Thr Gly Leu Lys Pro Gly Thr Glu Tyr Thr Val Ser Ile Tyr
        115                 120                 125

Gly Val Lys Gly Gly His Arg Ser Asn Pro Leu Ser Ala Glu Phe Thr
    130                 135                 140

Thr
145

<210> SEQ ID NO 68
```

```
<211> LENGTH: 146
<212> TYPE: PRT
<213> ORGANISM: Artificial Sequence
<220> FEATURE:
<223> OTHER INFORMATION: NIa protease fusion substrate with EAVTFQG
      recognition site

<400> SEQUENCE: 68
```

Met Gly Ser Ser His His His His His His Ser Ser Gly Leu Val Pro
1               5                   10                  15

Arg Gly Ser His Met Thr Thr Glu Ala Val Thr Phe Gln Gly Ser Thr
            20                  25                  30

Ala Ile Gly Met Lys Glu Thr Ala Ala Ala Lys Phe Glu Arg Gln His
        35                  40                  45

Met Asp Ser Pro Asp Leu Gly Thr Met Leu Pro Ala Pro Lys Asn Leu
    50                  55                  60

Val Val Ser Glu Val Thr Glu Asp Ser Leu Arg Leu Ser Trp Thr Ala
65                  70                  75                  80

Pro Asp Ala Ala Phe Asp Ser Phe Leu Ile Gln Tyr Gln Glu Ser Glu
                85                  90                  95

Lys Val Gly Glu Ala Ile Asn Leu Thr Val Pro Gly Ser Glu Arg Ser
            100                 105                 110

Tyr Asp Leu Thr Gly Leu Lys Pro Gly Thr Glu Tyr Thr Val Ser Ile
        115                 120                 125

Tyr Gly Val Lys Gly Gly His Arg Ser Asn Pro Leu Ser Ala Glu Phe
    130                 135                 140

Thr Thr
145

```
<210> SEQ ID NO 69
<211> LENGTH: 6
<212> TYPE: PRT
<213> ORGANISM: Artificial Sequence
<220> FEATURE:
<223> OTHER INFORMATION: NIa proteases P6-P1 recognition sequence
<220> FEATURE:
<221> NAME/KEY: VARIANT
<222> LOCATION: (2)...(2)
<223> OTHER INFORMATION: Xaa1 may be any amino acid
<220> FEATURE:
<221> NAME/KEY: VARIANT
<222> LOCATION: (3)...(3)
<223> OTHER INFORMATION: Xaa2 may be any amino acid
<220> FEATURE:
<221> NAME/KEY: VARIANT
<222> LOCATION: (5)...(5)
<223> OTHER INFORMATION: Xaa3 may be Ser or Gly

<400> SEQUENCE: 69
```

Glu Xaa Xaa Tyr Xaa Gln
1               5

```
<210> SEQ ID NO 70
<211> LENGTH: 10
<212> TYPE: PRT
<213> ORGANISM: Artificial Sequence
<220> FEATURE:
<223> OTHER INFORMATION: Synthetic peptide

<400> SEQUENCE: 70
```

Ser Glu Val Val Leu Phe Gln Ala Ser Ser
1               5                   10

```
<210> SEQ ID NO 71
```

```
<211> LENGTH: 10
<212> TYPE: PRT
<213> ORGANISM: Artificial Sequence
<220> FEATURE:
<223> OTHER INFORMATION: Synthetic peptide

<400> SEQUENCE: 71

Ser Glu Ala Val Tyr Thr Gln Gly Ser Ser
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthetic peptide

<400> SEQUENCE: 72

Ser Glu Asn Val Thr Phe Gln Gly Ser Ser
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)...(1)
<223> OTHER INFORMATION: 4-(4-dimethylaminophenylazo)benzoyl
<220> FEATURE:
<221> NAME/KEY: MOD_RES
<222> LOCATION: (11)...(11)
<223> OTHER INFORMATION: 5-[(2-aminoethyl)amino]naphthalene-1-sulfonic
      acid

<400> SEQUENCE: 73

Tyr Gly Glu Asn Val Thr Phe Gln Gly Ser Lys
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)...(2)
<223> OTHER INFORMATION: Xaa1 may be any amino acid
<220> FEATURE:
<221> NAME/KEY: VARIANT
<222> LOCATION: (4)...(4)
<223> OTHER INFORMATION: Xaa2 may be any amino acid
<220> FEATURE:
<221> NAME/KEY: VARIANT
<222> LOCATION: (5)...(5)
<223> OTHER INFORMATION: Xaa3 may be any amino acid
<220> FEATURE:
<221> NAME/KEY: VARIANT
<222> LOCATION: (7)...(7)
<223> OTHER INFORMATION: Xaa4 may be any amino acid

<400> SEQUENCE: 74

Glu Xaa Val Xaa Xaa Gln Xaa
1               5

<210> SEQ ID NO 75
<211> LENGTH: 7
<212> TYPE: PRT
```

```
<213> ORGANISM: Artificial Sequence
<220> FEATURE:
<223> OTHER INFORMATION: Synthetic peptide

<400> SEQUENCE: 75

Glu Val Val Leu Phe Gln Ala
 1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic peptide

<400> SEQUENCE: 76

Asn Thr Val Gln Phe Gln Ser
 1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic peptide

<400> SEQUENCE: 77

Glu Ala Val Gln Phe Gln Ser
 1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic peptide

<400> SEQUENCE: 78

Gly Val Val Ala Phe Gln Gly
 1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic peptide

<400> SEQUENCE: 79

Glu Ser Val Glu Phe Glu Ser
 1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic peptide

<400> SEQUENCE: 80

Glu Ala Val Tyr Thr Gln Gly
 1               5

<210> SEQ ID NO 81
<211> LENGTH: 7
<212> TYPE: PRT
<213> ORGANISM: Artificial Sequence
```

```
<220> FEATURE:
<223> OTHER INFORMATION: Synthetic peptide

<400> SEQUENCE: 81

Asp Met Val Tyr Phe Gln Ala
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic peptide

<400> SEQUENCE: 82

Glu Asn Val Thr Lys Gln Leu
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic peptide

<400> SEQUENCE: 83

Glu Met Val Thr Asn Gln Ser
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic peptide

<400> SEQUENCE: 84

Glu Asn Val Thr Phe Gln Gly Pro
1               5

<210> SEQ ID NO 85
<211> LENGTH: 8
<212> TYPE: PRT
<213> ORGANISM: Artificial Sequence
<220> FEATURE:
<223> OTHER INFORMATION: Synthetic peptide

<400> SEQUENCE: 85

Glu Asn Leu Tyr Gly Gln Gly Ser
1               5

<210> SEQ ID NO 86
<211> LENGTH: 8
<212> TYPE: PRT
<213> ORGANISM: Artificial Sequence
<220> FEATURE:
<223> OTHER INFORMATION: Synthetic peptide

<400> SEQUENCE: 86

Glu Thr Val Arg Phe Gln Gly Ser
1               5

<210> SEQ ID NO 87
<211> LENGTH: 10
<212> TYPE: PRT
<213> ORGANISM: Artificial Sequence
<220> FEATURE:
```

-continued

```
<223> OTHER INFORMATION: Synthetic peptide

<400> SEQUENCE: 87

Ser Glu Asn Val Thr Lys Gln Leu Ser Ser
 1               5                  10

<210> SEQ ID NO 88
<211> LENGTH: 10
<212> TYPE: PRT
<213> ORGANISM: Artificial Sequence
<220> FEATURE:
<223> OTHER INFORMATION: Synthetic peptide

<400> SEQUENCE: 88

Ser Glu Met Val Thr Asn Gln Ser Ser Ser
 1               5                  10
```